US008372399B2

(12) United States Patent
Stolen

(10) Patent No.: US 8,372,399 B2
(45) Date of Patent: Feb. 12, 2013

(54) BISPECIFIC ANTIBODIES AND AGENTS TO ENHANCE STEM CELL HOMING

(75) Inventor: Craig Stolen, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 11/469,081

(22) Filed: Aug. 31, 2006

(65) Prior Publication Data

US 2008/0057053 A1 Mar. 6, 2008

(51) Int. Cl.
A61K 39/395 (2006.01)
A61K 39/00 (2006.01)
A61K 38/19 (2006.01)
C12P 21/08 (2006.01)

(52) U.S. Cl. ............... 424/136.1; 424/130.1; 424/178.1; 424/182.1; 424/1.41; 424/1.53; 424/9.1; 424/85.1; 424/85.2; 424/85.5; 530/387.3

(58) Field of Classification Search ..................... None
See application file for complete search history.

(56) References Cited

U.S. PATENT DOCUMENTS

| | | | |
|---|---|---|---|
| 3,923,794 A | 12/1975 | Maruyama et al. |
| 4,676,980 A | 6/1987 | Segal et al. |
| 5,196,403 A | 3/1993 | Maraganore et al. |
| 5,474,563 A | 12/1995 | Myler et al. |
| 5,512,442 A | 4/1996 | Jalkanen et al. |
| 5,530,101 A | 6/1996 | Queen et al. |
| 5,545,806 A | 8/1996 | Lonberg et al. |
| 5,545,807 A | 8/1996 | Surani et al. |
| 5,569,825 A | 10/1996 | Lonberg et al. |
| 5,580,780 A | 12/1996 | Jalkanen et al. |
| 5,585,089 A | 12/1996 | Queen et al. |
| 5,611,016 A | 3/1997 | Fangmann et al. |
| 5,625,126 A | 4/1997 | Lonberg et al. |
| 5,633,425 A | 5/1997 | Lonberg et al. |
| 5,691,423 A | 11/1997 | Smith et al. |
| 5,718,892 A | 2/1998 | Keefer et al. |
| 5,736,137 A | 4/1998 | Anderson et al. |
| 5,776,456 A | 7/1998 | Anderson et al. |
| 5,843,439 A | 12/1998 | Anderson et al. |
| 5,935,598 A | 8/1999 | Sage et al. |
| 5,961,483 A | 10/1999 | Sage et al. |
| 6,066,321 A | 5/2000 | Jalkanen et al. |
| 6,152,141 A | 11/2000 | Stevens et al. |
| 6,185,953 B1 | 2/2001 | Sada et al. |
| 6,203,788 B1 | 3/2001 | Blaschuk et al. |
| 6,214,334 B1 | 4/2001 | Lee et al. |
| 6,261,549 B1 | 7/2001 | Fernandez et al. |
| 6,399,061 B1 | 6/2002 | Anderson et al. |
| 6,461,821 B1 | 10/2002 | Matsuzawa et al. |
| 6,541,116 B2 | 4/2003 | Michal et al. |
| 6,569,996 B1 | 5/2003 | Blaschuk et al. |
| 6,571,125 B2 | 5/2003 | Thompson |
| 6,586,187 B1 | 7/2003 | Gopalsamy et al. |
| 6,624,202 B2 | 9/2003 | Smith et al. |
| 6,663,863 B2 | 12/2003 | Horvath et al. |
| 6,667,034 B2 | 12/2003 | Palsson et al. |
| 6,682,734 B1 | 1/2004 | Anderson et al. |
| 6,806,255 B2 | 10/2004 | Doherty et al. |
| 6,907,238 B2 | 6/2005 | Leung |
| 6,914,144 B2 | 7/2005 | Pye |
| 6,962,969 B2 | 11/2005 | Blaschuk et al. |
| 6,982,286 B2 | 1/2006 | Smith et al. |
| 7,218,971 B2 | 5/2007 | Heil, Jr. et al. |
| 2002/0173521 A1 | 11/2002 | Smith et al. |
| 2002/0198189 A1 | 12/2002 | Besencon et al. |
| 2003/0125360 A1 | 7/2003 | Smith et al. |
| 2003/0171368 A1 | 9/2003 | Seitz et al. |
| 2003/0186967 A1 | 10/2003 | Kees et al. |
| 2004/0039441 A1 | 2/2004 | Rowland et al. |
| 2004/0063934 A1 | 4/2004 | Geneste et al. |
| 2004/0077638 A1 | 4/2004 | Geneste et al. |
| 2004/0077684 A1 | 4/2004 | De Corte et al. |
| 2004/0086519 A1 | 5/2004 | Kumar et al. |
| 2004/0106654 A1 | 6/2004 | Smith et al. |
| 2004/0176838 A1 | 9/2004 | Mucha et al. |
| 2004/0236108 A1 | 11/2004 | Smith et al. |
| 2004/0241162 A1 | 12/2004 | Berenson et al. |
| 2004/0259923 A1 | 12/2004 | Inoue et al. |
| 2005/0009835 A1 | 1/2005 | Thomas |
| 2005/0026917 A1 | 2/2005 | Kinney et al. |
| 2005/0059669 A1 | 3/2005 | Ajito et al. |

(Continued)

FOREIGN PATENT DOCUMENTS

WO  WO-9100360 A1  1/1991
WO  WO-93/01221 A1  1/1993

(Continued)

OTHER PUBLICATIONS

Roth and Yarmush, Annual Review Biomedical Engineering, 01:265-297, 1999.*
Losordo and Dimmeler, Circulation 190: 2692-2697, Jun. 2004.*
Cohn JN, Cardiovascular Drugs and Therapy 8: 119-122, Dec. 1994.*
Arvilommi et al., Eur J Immunol, 27(7):1794-1800, Jul. 1997.*
Lum et al., Experimental Hematology, 34(1):1-6, Jan. 2006.*
Blankenberg, Stefan, et al., "Adhesion molecules and atherosclerosis", *Atherosclerosis*, 170(2), (Oct. 2003), 191-203.
Christman, K. L., "Injectable Fibrin Scaffold Improves Cell Transplant Survival, Reduces Infarct Expansion, and Induces Neovasculature Formation in Ischemic Myocardium", *Journal of the American College of Cardiology*, 44(3), (Aug. 4, 2004), 654-660.
Dimmeler, S. , et al., "Unchain my heart: the scientific foundations of cardiac repair.", *J Clin Invest.*, 115 (3), (Mar. 2005),572-83.

(Continued)

*Primary Examiner* — Daniel E Kolker
*Assistant Examiner* — Stacey N MacFarlane
(74) *Attorney, Agent, or Firm* — Schwegman Lundberg & Woessner, P.A.

(57) ABSTRACT

A composition having a bispecific antibody which binds a stem cell specific antigen and a tissue, differentiated cell or condition associated antigen and an agent that enhances expression of the tissue, differentiated cell or condition associated antigen, is provided. Also provided are methods of using the bispecific antibodies and/or agents to enhance cell therapy.

19 Claims, No Drawings

U.S. PATENT DOCUMENTS

| | | | |
|---|---|---|---|
| 2005/0096360 A1 | 5/2005 | Salter-Cid et al. |
| 2005/0187611 A1 | 8/2005 | Ding et al. |
| 2005/0226873 A1 | 10/2005 | Del Priore |
| 2005/0267562 A1 | 12/2005 | Jones et al. |
| 2006/0015146 A1 | 1/2006 | Girouard et al. |
| 2006/0025438 A1 | 2/2006 | Salter-Cid et al. |
| 2006/0030575 A1 | 2/2006 | Danthi et al. |
| 2006/0041182 A1 | 2/2006 | Forbes et al. |
| 2006/0085063 A1 | 4/2006 | Shastri et al. |
| 2006/0128770 A1 | 6/2006 | Inoue et al. |
| 2006/0134071 A1 | 6/2006 | Ross et al. |
| 2006/0264643 A1 | 11/2006 | Patel |
| 2007/0003528 A1 | 1/2007 | Consigny et al. |
| 2008/0057027 A1 | 3/2008 | Stolen |
| 2008/0058922 A1 | 3/2008 | Stolen |

FOREIGN PATENT DOCUMENTS

| | | |
|---|---|---|
| WO | WO-98/30615 A1 | 7/1998 |
| WO | WO-9858669 A2 | 12/1998 |
| WO | WO/03/091398 * | 6/2003 |

OTHER PUBLICATIONS

Fujiyama, S., et al., "Bone marrow monocyte lineage cells adhere on injured endothelium in a monocyte chemoattractant protein-1-dependent manner and accelerate reendothelialization as endothelial progenitor cells", *Circulation Research*, 93(10), (Nov. 14, 2003), 980-9.

Gojo, S., "In vivo cardiovasculogenesis by direct injection of isolated adult mesenchymal stem cells", *Experimental Cell Research*, 288(1), (Aug. 1, 2003), 51-59.

Haider, H., et al., "Bone marrow stem cell transplantation for cardiac repair.",. *Am J Physiol Heart Circ Physiol.*, 288(6) Jun. 2005), H2557-67.

Hofmann, M., et al., "Monitoring of bone marrow cell homing into the infarcted human myocardium", *Circulation*, 111(17), (May 3, 2005), 2198-202.

Houghton, Jeanmarie, et al., "Gastric Cancer Originating from Bone Marrow-Derived Cells", *Science*, 306(5701), (Nov. 26, 2004), 1568-1571.

Lum, L. G., et al., "Targeting of Lin-Sca+ hematopoietic stem cells with bispecific antibodies to injured myocardium", *Blood Cells Mol Dis.*, 32(1), (Jan.-Feb. 2004), 82-7.

McGowan, N. W., et al., "Cytokine-activated endothelium recruits osteoclast precursors", *Endocrinology*, 142(4), (Apr. 2001), 1678-81.

Menasche, P., "Cell transplantation in myocardium", *The Annals of Thoracic Surgery*, 75(6), (Jun. 2003), S20-S28.

Minami, E., "Skeletal muscle meets cardiac muscle. Friends or foes?" *J Am Coll Cardiol.*, 41(7), (Apr. 2, 2003), 1084-6.

Petit, I., et al., "G-CSF induces stem cell mobilization by decreasing bone marrow SDF-1 and up-regulating CXCR4", *Nature Immunology*, 3(7), (Jul. 2002), 687-94.

Sata, M., et al., "Inflammation, angiogenesis, and endothelial progenitor cells: how do endothelial progenitor cells find their place?", *Journal of Molecular and Cellular Cardiology*, 36(4), (Apr. 2004), 459-463.

Schachinger, V., et al., "Transplantation of progenitor cells and regeneration enhancement in acute myocardial infarction: final one-year results of the TOPCARE-AMI Trial", *Journal of the American College of Cardiology*, 44(8), (Oct. 19, 2004), 1690-1699.

Tambara, K., "Transplanted Skeletal Myoblasts Can Fully Replace the Infarcted Myocardium When They Survive in the Host in Large Numbers", *Circulation*, 108 [Suppl I], (2003), II-259-II-263.

Vermeulen, M., et al., "Role of Adhesion Molecules in the Homing and Mobilization of Murine Hematopoietic Stem and Progenitor Ce", *Blood*, 92(3), (Aug. 1, 1998), 894-900.

Voermans, C., et al., "Adhesion molecules involved in transendothelial migration of human hematopoietic progenitor cells", *Stem Cells*, 18(6), (2000), 435-43.

Wollert, K. C., et al., "Clinical applications of stem cells for the heart", *Circulation Research*, 96(2), (Feb. 4, 2005), 151-63.

Zeiffer, U., et al., "Neointimal smooth muscle cells display a proinflammatory phenotype resulting in increased leukocyte recruitment mediated by P-selectin and chemokines", *Circulation Research*, 94(6), (Apr. 2, 2004), 776-84.

Zhu, H., et al., "The Role of the Hyaluronan Receptor CD44 in MSC Migration in the Extracellular Matrix", *Stem Cells*, Epub ahead of print, (Nov. 23, 2005), 1-32.

Kreitman, R. J., "Recombinant toxins for the treatment of cancer.", *Curr Opin. Mol Ther.*, 5(1), (Feb. 2003),44-51.

Cooke, B. M, et al., "Cytoadhesion and Falciparum Malaria: Going with the Flow", *Parasitology Today*.vol. 11(8), (1995), 282-287.

Corey, J. M., et al., "Substrate patterning: an emerging technology for the study of neuronal behavior", *Experimnetal Neurology 184*, (2003), S89-S96.

Daniella, K., "Present Capabilities & Future Disposable Bioreactors", *Wave Biotech Presentation*, (2004), 35 pgs.

Divietro, J. A, et al., "Immobilized IL-8 triggers Progressive Activation of Neutrophils Rolling In Vitro on P-Selection and Intercellular Adhesion Molecule-1", *Journal of Immunology*. vol. 167, (2001), 4017-4025.

Hinds, M. T, et al., "Local hemodynamics affect monocytic cell adhesion to a three-dimensional flow model coated with E-selection", *Journal of Biomechanics*. vol. 34, (2001), 95-103.

Tsuchiya, K., et al., "Effects of cell adhesion molecules on adhesion of chondrocytes, ligament cells and mesenchymal stem cells", *Materials Science and Engineering*.vol. C17, (2001), 79-82.

Greenberg, et al., "Blood", *95*, (2000), 478-486.

"U.S. Appl. No. 11/469,064, Final Office Action mailed Jun. 9, 2009", 11 pgs.

"U.S. Appl. No. 11/469,064, Response filed May 29, 2009 to Non Final Office Action mailed Feb. 20, 2009", 12 pgs.

"U.S. Appl. No. 11/469,064, Response filed Oct. 21, 2009 to Final Office Action mailed Jun. 9, 2009", 17 pgs.

"U.S. Appl. No. 11/469,092 Non-Final Office Action mailed Jun. 29, 2009", 32 pgs.

"U.S. Appl. No. 11/469,092, Response filed May 29, 2009 to Final Office Action mailed Jan. 30, 2009", 17 pgs.

"U.S. Appl. No. 11/469,092, Response filed Oct. 29, 2009 to Non Final Office Action mailed Jun. 29, 2009", 14 pgs.

Stroock, et al., "Science", *295*, (2002), 647-651 pgs.

"U.S. Appl. No. 11/469,092, Response filed Mar. 16, 2010 to Final Office Action maied Dec. 17, 2009", 16 pgs.

"U.S. Appl. No. 11/469,092, Final Office Action mailed Mar. 20, 2008", 22 pgs.

"U.S. Appl. No. 11/469,092, Response filed May 20, 2008 to Final Office Action mailed Mar. 20, 2008", 13 pgs.

"U.S. Appl. No. 11/469,092, Non-Final Office Action mailed Jul. 13, 2010", 20 pgs.

"U.S. Appl. No. 11/469,092, Non-Final Office Action mailed Aug. 20, 2008", 20 pgs.

"U.S. Appl. No. 11/469,092, Non-Final Office Action mailed Aug. 27, 2007", 19 pgs.

"U.S. Appl. No. 11/469,092, Response filed Jul. 25, 2007 to Restriction Requirement mailed Jun. 25, 2007", 15 pgs.

"U.S. Appl. No. 11/469,092, Response filed Dec. 27, 2007 to Non-Final Office Action mailed Aug. 27, 2007", 12 pgs.

"U.S. Appl. No. 11/469,092, Restriction Requirement mailed Jun. 25, 2007", 9 pgs.

"U.S. Appl. No. 11/469,064, Non-Final Office Action mailed Jan. 24, 2008", 7 pgs.

"U.S. Appl. No. 11/469,064, Response filed Apr. 24, 2008 to Non-Final Office Action mailed Jan. 24, 2008", 11 pgs.

"U.S. Appl. No. 11/469,064, Final Office Action mailed on Aug. 21, 2008", 6 pgs.

"Present Capabilities & Future Disposable Bioreactors", Wave Biotech, LLC Presentation, (2004), 35 pgs.

Zhao, L. C., "Cell Adhesion: Characterization of Adhesive Forces and Effect of Topography", Master Thesis, Univeristy of Florida, (2000), 88 pgs.

"U.S. Appl. No. 11/469,064, Response filed Sep. 28, 2010 to Final Office Action mailed May 28, 2010", 15 pgs.

"U.S. Appl. No. 11/4469,092, Response filed Mar. 16, 2010 to Final Office Action mailed Dec. 17, 2009", 16 pgs.

"U.S. Appl. No. 11/469,064, Final Office Action mailed May 28, 2010", 11 pgs.

"U.S. Appl. No. 11/469,064, Non-Final Office Action mailed Feb. 20, 2009", 8 pgs.

"U.S. Appl. No. 11/469,064, Non-Final Office Action mailed Jan. 12, 2010", 8 pgs.

"U.S. Appl. No. 11/469,064, Response filed Nov. 20, 2008 to Final Office Action mailed Aug. 21, 2008", 12 pgs.

"U.S. Appl. No. 11/469,064, Response filed May 12, 2010 to Non Final Office Action mailed Jan. 12, 2010", 14 pgs.

"U.S. Appl. No. 11/469,092, Final Office Action mailed Dec. 17, 2009", 32 Pgs.

"U.S. Appl. No. 11/469,092, Final office Action Received on Jan. 30, 2009", 33 pgs.

"U.S. Appl. No. 11/469,092, Response filed Nov. 19, 2008 to Non Final Office Action mailed Aug. 20, 2008", 19 pgs.

Bonanno, G., et al., "Human cord blood CD133+ cells immunoselected by a clinical-grade apparatus differentiate in vitro into endothelial-and cardiomyocyte-like cells", *Transfusion*, (Feb. 2000), 280-289.

Brown, A. R, et al., "Large-Eddy Simulation of Neutral Turbulent Flow Over Rough Sinusoidal Ridges", *Boundary-Layer Meteorology*, 98(3), (Mar. 2001), 411-441.

Ceafalan, L., et al., "Expression of stem cell markers on fetal and tumoral human liver cells in primary culture", *Rev Med Chir Soc Med Nat Iasi*, (2005), 96-104.

Gradeck, M., et al., "Wall shear measurements inside corrugated channels using the electrochemical technique", *Experiments in Fluids*, 24(1), (Jan. 1998), 17-26.

Hsu, H, et al., "Hematopoietic stem cells express Tie-2 receptor in the murine fetal liver", *Blood*, (Dec. 2000), 3757-3762.

Jaatinen, T., et al., "Isolation of hematopoietic stem cells from human cord blood.", *Curr Protoc Stem Cell Biol., Chapter 2*, (Jun. 2007), Unit 2A.2.

Kerfoot, C., et al., "Cerebral cortical dysplasia: giant neurons show potential for increased excitation and axonal plasticity", *Dev Neurosci*, (Nov. 1999), 260-270.

Martinez, O. M., et al., "CD30 expression identifies a functional alloreactive human T-lymphocyte subset", *Transplantation*, (May 1998), 1240-1247.

Nathan, Carl, et al., "Cytokines in Context", *Journal of Cell Biology* vol. 113 No. 5, (Jun. 1991), 981-986.

Oh, J. D., et al., "Overexpression of neurotrophin receptor p75 contributes to the excitotoxin-induced cholinergic neuronal death in rat basal forebrain", *Brain Res.*, (Jan. 2000), 174-185

Salmi, Marko, et al., "Homing of Mucosal Leukocytes to Joints", *J. Clin. Invest.*, (May 1997) 2165-2172

Salmi, Marko, et al., "Human Vascular Adhesion Protein-1 (VAP-1) Plays a Critical Role in Lymphocyte-Endothelial Cell Adhesion Cascade Under Shear", *Circ. Res 2000;86*, (2000), 1245-1251

Scherer, S. E., et al., "Expression and regulation of kainate and AMPA receptors in the rat neural tube", *J. Neurosci Res*, (May 1998), 356-368.

"U.S. Appl. No. 11/469,064, Non Final Office Action mailed Feb. 7, 2011", 18 pgs.

"U.S. Appl. No. 11/469,092, Final Office Action mailed Dec. 10, 2010", 23 pgs.

"U.S. Appl. No. 11/469,092, Response filed Nov. 12, 2010 to Non Final Office Action mailed Jul. 13, 2010", 15 pgs.

Frangogiannis, N. G., et al., "The Inflammatory Response in Myocardial Infarction", Cardiovascular Research, 53(1), (Jan. 2002), 31-47.

Granger, D. Neil, et al., "Recruitment of Inflammatory and Immune Cells in the Gut: Physiology and Pathophysiology", Physiology of the Gastrointestinal Tract, Fourth Edition, (2006), 1137-1162.

Hahne, Michael, et al., "Five Tumor Necrosis Factor-inducible Cell Adhesion mechanisms on the Surface of Mouse Endothelioma Cells Mediate the Binding of Leukocytes", The Journal of Cell Biology, vol. 121, No. 3, (May 1993), 655-664.

Janeway, Charles A, et al., "Chapter 10: Host Defense Against Infection", Immuno Biology: The Immune System in Health and Disease, Fourth Edition, (1999), 376-377.

Karupiah, Gunasegaran, "Cytokines and Chemokines in Infectious Diseases Handbook", Immunology and Cell Biology (2003) 81, 3 pgs, http://www.nature.com/icb/journal/v81/n6/full/icb200371a.html, downloaded Apr. 28, 2011.

Mako, V, et al., "Proinflammatory activation pattern of human umbilical vein endothelial cells induced by IL-1β, TNF-a, and LPS", Cytometry A, 77(10), (Oct. 2010), 962-70.

Montgomery, Kevin F, et al., "Activation of endothelial-leukocyte molecule 1 (ELAM-1) gene transcription", Proc. Natl. Acad. Sci. USA, vol. 88, Medical Sciences, (Aug. 1991), 6523-6527.

Thompson, Angus W, "The Cytokine Handbook, Third Edition", (Jul. 1, 1998), 5 pgs, http://www.amazon.com/Cytokine-Thompson.dp/0126896623, Downloaded Apr. 28, 2011.

"U.S. Appl. No. 11/469,064, Final Office Action mailed Aug. 4, 2011", 20 pgs.

"U.S. Appl. No. 11/469,064, Response filed Jun. 7, 2011 to Non Final Office Action mailed Feb. 7, 2011", 21 pgs.

"U.S. Appl. No. 11/469,092, Advisory Action mailed Jun. 11, 2008", 3 pgs.

"U.S. Appl. No. 11/469,092, Response filed May 10, 2011 to Final Office Action mailed Feb. 10, 2010", 16 pgs.

"Oregovomab: anti-CA-125 monoclonal antibody B43.13—AltaRex, B43.13, MAb B43.13, monoclonal antibody B43.13", Drugs R D., 7(6), (2006), Abstract.

Aluigi, M., et al., "Nucleofection is an efficient nonviral transfection technique for human bone marrow-derived mesenchymal stem cells", Stem Cells, 24(2), (Feb. 2006), 454-61.

Carpene, C., "Chapter 12—Amine Oxidases in Adipose Tissue-Related Disorders", In: Copper Amine Oxidases: Structures, Catalytic Mechanisms and Role in Pathophysiology / Edition 1, CRC Press, (Jun. 2009), 177-194.

Chen, X., et al., "Chemokines and chemokine receptors as novel therapeutic targets in rheumatoid arthritis (RA): inhibitory effects of traditional Chinese medicinal components.", Cell Mol Immunol., 1(5), (Oct. 2004), 336-42.

Chen, Y. F, et al., "A systematic review of the effectiveness of adalimumab, etanercept and infliximab for the treatment of rheumatoid arthritis in adults and an economic evaluation of their cost-effectiveness.", Health Technol Assess, 10(42), (Nov. 2006), Abstract.

Ellis, Jonathan, et al., "Engineered anti-CD38 monoclonal antibodies for immunotherapy of multiple myeloma", The American Association of Immunologists, 155(2), (1995), 925-937.

Goldmacher, V. S, et al., "Anti-CD38-blocked ricin: an immunotoxin for the treatment of multiple myeloma", Blood, 84(9), (Nov. 1, 1994), 3017-25.

Gordon, E. J, et al., "Prolonged survival of rat islet and skin xenografts in mice treated with donor splenocytes and anti-CD154 monoclonal antibody.", Diabetes, 47(8), (Aug. 1998), 1199-206.

Gordon, E. J, et al., "Rat Xenograft Survival in Mice Treated with Donor-Specific Transfusion and Anti-CD154 Antibody is Enhanced by Elimination of Host CD4+ Cells", Transplantation, 71(2), (Jan. 27, 2001), 319-327.

Greenlee, J. E, "Progressive multifocal leucoencephalopathy in the era of natalizumab: a review and discussion of the implications", Int MS J., 13(3), (Nov. 2006), Abstract.

Guo, Z., et al., "Blockade of CD4 Molecules by Nondepleting anti-CD4 Monoclonal Antiodies Prevents Xenogeneic Pig Islet Graft Rejecting and Recurrence of Autoimmune Diabetes.", Transplantation, vol. 67 (09), (May 15, 1999), 29-29.

Guo, Z. G, et al., "Effect of Therapy with Non-Depleting Anti-CD4 Monoclonal Antibody and CTLA4Ig on Allogeneic Islet Graft Survival in Autoimmune Diabetic Nod Mice", Transplantation, vol. 69(8), (Apr. 27, 2000), 659-659.

Gupta, A. K, et al., "Efalizumab in the treatment of psoriasis", J Cutan Med Surg., 10(2), (Mar.-Apr. 2006), Abstract.

Hadri, K. E., et al., "Semicarbazide-Sensitive Amine Oxidase in Vascular Smooth Muscle Cells: Differentiation-Dependent Expression and Role in Glucose Uptake", Arteriosclerosis, Thrombosis, and Vascular Biology, 22, (2002), 89-94.

Ho, V. T, et al., "The history and future of T-cell depletion as graft-versus-host disease prophylaxis for allogeneic hematopoietic stem cell transplantation", Blood, 98(12), (Dec. 1, 2001), 3192-204.

Hoy, S. M, et al., "Panitumumab: in the treatment of metastatic colorectal cancer.", Drugs, 66(15), (2006), Abstract.

Jones, H. A, "Inflammation imaging", Proc Am Thorac Soc., 2(6), (2005), 545-8, 513-4.

Kofler, S., et al., "Role of cytokines in cardiovascular diseases: a focus on endothelial responses to inflammation", Clin Sci (Lond), 108(3), (Mar. 2005), Abstract.

Lakshmipathy, U., et al., "Efficient transfection of embryonic and adult stem cells", Stem Cells, 22(4), (2004), 531-43.

Larsen, C. P., et al., "Long-term acceptance of skin and cardiac allografts after blocking CD40 and CD28 pathways.", Nature. 381(6581), (1996), 434-8.

Lehmann, M., et al., "Anti-CD4 Monoclonal Antibody-Induced Allograft Tolerance in Rats Despite Persistence of Donor-Reactive T Cells", Transplantation (Baltimore), 64(8), (Oct. 27, 1997), 1181-1187.

Lehnert, A. M, et al., "Pancreatic islet xenograft tolerance after short-term costimulation blockade is associated with increased CD4+ T cell apoptosis but not immune deviation", Transplantation, 69(6), (Mar. 27, 2000), 1176-85.

Lu, X., et al., "Requirement of CD4 Cells for Induction and Maintenance of Unresponsiveness in Islet Xenografted Mice.", Xenotransplantation, 5(3), (Aug. 1998), 207-214.

Maguire, A. M, et al., "Allogeneic bone marrow transplant improves outcome for juvenile myelomonocytic leukaemia", J Paediatr Child Health, 38(2), (Apr. 2002), Abstract.

Martelius, T., et al., "Inhibition of semicarbazide-sensitive amine oxidases decreases lymphocyte infiltration in the early phases of rat liver allograft rejection", Int J Immunopathol Pharmacol., 21(4), (Oct.-Dec. 2008), 911-20.

Marttila-Ichihara, F., et al., "Vascular Amine Oxidases Are Needed for Leukocyte Extravasation Into Inflamed Joints in Vivo", Arthritis & Rheumatism, 54(9), (Sep. 2006), 2852-2862.

Mizia-Stec, K., "Cytokines and adhesive molecules in detection of endothelial dysfunction", Pharmacological Reports, 58, (2006), 21-32.

Nash, G. B, et al., "The local physicochemical environment conditions the proinflammatory response of endothelial cells and thus modulates leukocyte recruitment.", FEBS Lett., 569(1-3), (Jul. 2, 2004), Abstract.

O'Connor, P., "Natalizumab and the role of alpha 4-integrin antagonism in the treatment of multiple sclerosis", Expert Opin Biol Ther., 7(1), (Jan. 2007), Abstract.

O'Rourke, A. M, et al., "Benefit of inhibiting SSAO in relapsing experimental autoimmune encephalomyelitis", J Neural Transm., 114(6), (2007), 845-9.

Piro, M., et al., "Endothelium and inflammation.", Panminerva Med., 47(2), (Jun. 2005), Abstract.

Riederer, P., et al., "Clinical applications of MAO-inhibitors", Curr Med Chem., 11(15), (Aug. 2004), Abstract.

Stolen, C. M, et al., "Absence of the endothelial oxidase AOC3 leads to abnormal leukocyte traffic in vivo.", Immunity, 22(1), (Jan. 2005), 105-15.

Stolen, C. M, et al., "Origins of serum semicarbazide-sensitive amine oxidase", Circ Res., 95(1), (Jul. 9, 2004), 50-7.

Stolen, C. M, et al., "Semicarbazide-sensitive amine oxidase overexpression has dual consequences: insulin mimicry and diabetes-like complications", FASEB J., 18(6), (Apr. 2004), 702-4.

Tousoulis, D., et al., "Endothelial function and inflammation in coronary artery disease.", Heart, 92(4), (Apr. 2006), 441-4.

Wognum, A. W, et al., "Identification and isolation of hematopoietic stem cells", Arch Med Res., 34(6), (Nov.-Dec. 2003), 461-75.

Wu, T., et al., "Cardiovascular disease in diabetic nephropathy patients: cell adhesion molecules as potential markers?", Vasc Health Risk Manag., 1(4), (2005), 309-16.

Yraola, F., et al., "Structure-activity relationships of SSAO/VAP-1 arylalkylamine-based substrates", ChemMedChem., 4(4), (Apr. 2009), 495-503.

"U.S. Appl. No. 11/469,064 , Response filed Dec. 5, 2011 to Final Office Action mailed Aug. 4, 2011", 18 pgs.

Arvilommi, A. M., et al., "Lymphocyte Binding to Vascular Endothelium in Inflamed Skin Revisited: A Central Role for Vascular Adhesion Protein-1 (VAP-1)", European Journal of Immunoloy, 26(4), (1996), 825-833.

Benita, S., et al., "Characterization of drug-loaded poly(d,l-lactide) microspheres", J Pharm Sci, 73(12). (Dec. 1984), 1721-1724.

Bertini, V. et al., "Alkylarnino Derivatives of 4-Aminornethylpyridine as inhibitors of Copper-Containing Amine Oxidases", J. Med. Chem., 48(3), (2005), 664-670.

Chou, T. C., et al., "Quantitative analysis of dose-effect relationships: the combined effects of multiple drugs or enzyme inhibitors", Advances in Enzyme Regulation, 22, (1984), 27-55.

Dostert, P., et al., "Inhibition of Semicarbazide-Sensitive Amine Oxidase by Monoamine Oxidase B Inhibitors From the Oxazolidinone Series", Journal of Pharmacy and Pharmacology, 36(11), (1984), 782-785.

Gombotz, W. R., et al., "Protein Release from Alginate Matrices", Advanced Drug Delivery Reviews, 31(3), (1998), 267-285.

Heller, J., et al., "Poly(ortho esters): Synthesis, Characterization, Properties and Uses", Advanced Drug Delivery Reviews, 54 (7), (2002), 1015-1039.

Hou, W. C, et al., "Inhibitory activities of semicarbazide-sensitive amine oxidase and angiotensin converting enzyme of pectin hydroxamic acid.", J Agric Food Chem., 51(21), (Oct. 8, 2003), 6362-6366.

Kirten, C. M., et al., "Function-Blocking Antibodies to Human Vascular Adhesion Protein-1: A Protein Anti-Inflammatory Therapy", Eur. J. Immunol., 35, (2005), 3119-3130.

Koskinen, K., et al., "Granulocyte Transmigration Through the Endothelium is Regulated by the Oxidase Activity of Vascular Adhesion Protein-1 (VAP 1)", Blood, 103(9), (2004), 3388-3395.

Lazar, L., et al., "Synthesis of Hydrazing Alcohols With Anti-Inflammatory Activity", Acta Pharma. Hungarica, 74(11, (2004), 11-18.

Lizcano, J. M, et al., "Amine Oxidase Activities in Chemically Induced Mammary Cancer in the Rat", J Neural Transco Suppl., 32, (1990), 323-326.

Mathiowitz, E., et al., "Morphology of polyanhydride microsphere delivery systems", Scanning Microscopy, 4(2), (Jun. 1990), 329-340.

Mathiowitz, E., "Novel Microcapsules for Delivery Systems", Reactive Polymers, Ion Exchangers, Sorbents, 6(2-3), (1987), 275-293.

Mathiowitz, E., et al., "Polyanhydride microspheres as drug carriers I. Hot-melt microencapsulation", Journal of Controlled Release, 5(1), (Jun. 1987), 13-22.

Mathiowitz, E., et al., "Polyanhydride Microspheres as Drug Carriers. II. Microencapsulation by Solvent Removal", Journal of Applied Polymer Science, 35, (1988), 755-774.

Mathiowitz, E., et al., "Polyanhydride microspheres. IV. Morphology and characterization of systems made by spray drying", Journal of Applied Polymer Science, 45(1), (1992), 125-134.

Megeed, Z., et al., "Controlled Release of Plasmid DNA From a Genetically Engineered Silk-Elastinlike Hydrogel", Pharmaceutical Research, 19(7), (2002), 954-959.

Obata, T., et al., "Evidence for Existence of Immobilization. Stress-Inducible Semicarbazide-Sensitive Amine Oxidase Inhibitor in Rat Brain Cytosol", Neuroscience Letters, 296(1), (2000), 58-60.

Roy, K., et al., "Gene Delivery with In-situ Crosslinking Polymer Networks Generates Long-Term Systemic Protein Expression", Molecular Therapy, 7, (2003), 401-408.

Salmi, M., et al., "Induction and Function of Vascular Adhesion Protein-1 at Sites of Inflammation", Journal of Experimental Medicine, 178(6), (1993), 2255-2260.

Stolen, C. M, et al., "Semicarbazide sensitive amine oxidase overexpression has dual consequences: insulin mimicry and diabetes-like complications", FASEB J., 18(6), (Apr. 2004), 702-4.

Wang, E. Y, et al., "Design, synthesis, and biological evaluation of semicarbazide-sensitive amine oxidase (SSAO) inhibitors with anti-inflammatory activity", J. Med. Chem., 49(7), (Apr. 2006), 2166-73.

Yegutkin, G. G., et al., "A Peptide Inhibitor of Vascular Adhesion Protein-1 (VAP-1) Blocks Leukocyte-Endothelium Interactions Under Shear Stress", European Journal of Immunology, 34(8), (2004), 2276-2285.

"U.S. Appl. No. 11/469,064, Non Final Office Action mailed Mar. 29, 2012", 17 pgs.

Sherif, H. M, "In search of a new therapeutic target for the treatment of genetically triggered thoracic aortic aneurysms and cardiovascular conditions: insights from human and animal lathyrism", Interact Cardiovasc Thorac Surg., 11(3), (Sep. 2010), 271-6.

"U.S. Appl. No. 11/469,064, Final Office Action mailed Sep. 5, 2012", 12 pgs.

* cited by examiner

BISPECIFIC ANTIBODIES AND AGENTS TO ENHANCE STEM CELL HOMING

FIELD OF THE INVENTION

This document relates generally to therapy of living tissue which employs, but not by way of limitation, the use of bispecific antibodies, agents that enhance the expression of tissue, cell or condition associated antigens, or both, in methods to enhance localization and retention of cells in cell therapy.

BACKGROUND

Stem/progenitor cell transplantation has emerged as a potential therapeutic modality for numerous conditions. For cardiac applications, cell injections have usually been accomplished under direct control through multiple epicardial punctures. However, to reduce the invasiveness of the procedure, percutaneous approaches are undergoing development. In the setting of these percutaneous techniques, the transvenous approach, using a specifically dedicated coronary sinus catheter, is particularly attractive because of its greater simplicity compared with the endoventricular route. Initial studies have established the effectiveness of bone marrow stem cell (BMC) transvenous transfer into the myocardium (Thomson et al., *J. Am. Coll. Cardiol.*, 34:7514 (2002)). Intracoronary injections of bone marrow mononuclear cells concomitant with angioplasty at the acute stage of myocardial infarction (MI) have also shown promising results (Strauer et al., *Circ.*, 106:1913 (2002); Assmus et al., *Circ.*, 106:3009 (2002)).

More recent efficacy data from preliminary studies in which patients with an acute MI were treated by application of BMC showed a 7-9% improvement in global LV ejection fraction, as well as improvements in regional wall motion, perfusion, and LV end systolic volumes four to six months after intracoronary BMC transplantation (see Wollert et al., *Circ. Res.*, 96:151 (2005); Haider et al., *Am. J. Physiol. Circ. Physiol.*, 288:H2557 (2005); Dimmeler et al., *J. Clin. Investig.*, 115:572 (2005)). In particular, the final one-year results of the TOPCARE-AMI trial, demonstrated a sustained improvement of LV function, reduced infarct size, and an absence of reactive hypertrophy after intracoronary BMC transplantation, suggesting functional regeneration of the infarcted ventricles and a prevention of remodeling (Schachinger et al., *J. Am. Coll. Cardiol.*, 44:1690 (2004)). These findings are despite the observation that only 1.3-2.6% of the transplanted BMC are ultimately retained in the infarct after intracoronary transfer (Hofmann et al., *Circ.*, 111:2198 (2005)).

However, most transplanted cells never initially engraft (Christman et al., *J. Am. Coll. Cardiol.*, 44:465 (2004)), very few are viable within one week post injection (Gojo et al., *Exp. Cell. Res.*, 288:51 (2003)), and the vast majority of transplanted cells die (Minami et al., *J. Am. Coll. Cardiol.*, 41:1084 (2003)). Thus, regardless of the route of delivery, cell number and cell death remain major limitations of cell transplantation. For instance, it is uncertain whether multiplication of those that have survived can replace the high attrition rate.

What is needed is an improved method to enhance homing, engraftment and retention of transplanted therapeutic cells.

SUMMARY OF THE INVENTION

Cell therapy has the potential to treat many pathological conditions, although a major problem with cell treatment modalities is poor stem cell homing, engraftment and retention at the site of interest. The invention provides methods and compositions for enhancing (increasing) targeting of donor cells, e.g., stem cells, to a specific site and optionally increasing their retention at that site by using bispecific antibodies with specificity for both stem cells and the target tissue or cell, or site, and/or an agent that enhances the expression of an antigen associated with the tissue, cell or site.

The invention provides a method of enhancing localization and retention of stem cells. The method includes administering (delivering) to a mammal in need of cell therapy an effective amount of bispecific antibodies which bind a stem cell specific antigen and a tissue, differentiated cell or condition associated antigen, an agent or treatment that enhances expression of the tissue, differentiated cell or condition associated antigen, and donor stem cells. In one embodiment, the invention provides a method for targeting stem cells to a site of injury or inflammation. The method includes administering to a mammal an effective amount of bispecific antibodies which bind a stem cell specific antigen and an antigen associated with injury or inflammation, an agent or treatment that enhances expression of the injury or inflammation associated antigen, and donor stem cells having the stem cell specific antigen, where the agent or treatment is locally administered. In one embodiment, the agent or treatment is a cytokine, growth factor, induction of hypoxia, pacing with or without synchrony, heat, reactive oxygen species or ozone. In another embodiment, the invention provides a method for targeting stem cells to a selected location in a mammal. The method includes administering to a mammal in need of cell therapy an effective amount of bispecific antibodies which bind a stem cell specific antigen and a tissue or differentiated cell specific antigen, and donor stem cells, where the tissue or differentiated cell specific antigen is specific for neuronal cells, microglial cells, pancreatic cells, cartilage, or endothelial cells.

In one embodiment, bispecific antibodies can be used to target proteins (e.g., cytokines) and pharmaceuticals (drugs) to specific tissues, differentiated cells or sites in vivo. In particular, a selected protein or drug may be attached to the Fc portion of a bispecific antibody. For instance, the selected protein or drug may enhance cell engraftment, survival, differentiation, or any combination thereof. As a result of the binding of the bispecific antibody to a tissue, differentiated cell or condition associated antigen in vivo, the linked protein or drug is also delivered to the target region. In one embodiment, vascular endothelial growth factor (VEGF) is attached to a bispecific antibody, e.g., via a cleavable linker, and once delivered to a target region, promotes angiogenesis. In another embodiment, the selected, attached protein or drug inhibits apoptosis. In yet another embodiment, the selected, attached protein or drug enhances or activates adhesion molecule expression on endothelial cells, thereby enhancing engraftment, extravasation, or both, of the donor cells.

In one embodiment, the stem cell specific antigen includes but is not limited to CD34, CD133, ABCG2, Sca-1, Stro-1, Nestin, PSA-NCAm, p75 neurotrophin, c-kit, kit, CD30, and the like. In one embodiment, the tissue, cell or site specific antigen includes but is not limited to inflammatory markers or adhesion molecules, e.g., vascular adhesion protein-1 (VAP-1), P-selectin, E-selectin, intercellular adhesion molecule (ICAM), vascular cellular adhesion molecule (VCAM), vascular leukocyte adhesion (VLA), etc.; scar tissue components, e.g., collagen; or tissue or cell specific antigens, such as antigens specific for cardiac tissue, pancreatic tissue, e.g., insulin receptor, neuronal cells, e.g., p97 or transferrin receptor, microglial cells, and synovial fluid secreting cells. In one embodiment, the methods of the invention are used for the repopulation of destroyed cells, for instance in an organ in need of repair such as kidneys, liver, heart, lungs, intestines and the like, which may be highly advantageous in patients suffering from damage due to spinal cord trauma, diabetes, organ damage, or Alzheimer's disease. The stem cells are contacted with an antibody which is specific for the stem cells and for the organ or physiological site of interest, and administered to a host organism, e.g., a mammal. When the stem cells come in contact with the tissue in need of repair or site of interest, the stem cells repopulate the region of the tissue or site and optionally differentiate into functional cells due to influences of the environment. The invention is thus widely applicable to any condition amenable to cell therapy, e.g., treatment of heart disease, diabetes, Alzheimer's disease, spinal cord damage, arthritis, etc.

The invention includes the use of agents or treatments that enhance expression of adhesion molecules on donor cells and/or endogenous tissue or cells, such as intermittent hypoxia, cytokines, shock waves and pacing, and devices useful to deliver antibodies, donor cells, agents, or a combination thereof. In one embodiment, the invention provides a composition including a bispecific antibody which binds a stem cell specific antigen and a tissue, differentiated cell or condition associated antigen; and an agent that enhances expression of the tissue, differentiated cell or condition associated antigen.

DETAILED DESCRIPTION OF THE INVENTION

Definitions

A "vector" or "construct" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a sequence of interest for gene therapy. Vectors include, for example, transposons and other site-specific mobile elements, viral vectors, e.g., adenovirus, adeno-associated virus (AAV), poxvirus, papillomavirus, lentivirus, herpesvirus, foamivirus and retrovirus vectors, and including pseudotyped viruses, liposomes and other lipid-containing complexes, and other macromolecular complexes capable of mediating delivery of a polynucleotide to a host cell, e.g., DNA coated gold particles, polymer-DNA complexes, liposome-DNA complexes, liposome-polymer-DNA complexes, virus-polymer-DNA complexes, e.g., adenovirus-polylysine-DNA complexes, and antibody-DNA complexes. Vectors can also comprise other components or functionalities that further modulate gene delivery and/or gene expression, or that otherwise provide beneficial properties to the cells to which the vectors will be introduced. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

A "recombinant viral vector" refers to a viral vector comprising one or more heterologous genes or sequences. Since many viral vectors exhibit size constraints associated with packaging, the heterologous genes or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying genes necessary for replication and/or encapsidation). Modified viral vectors in which a polynucleotide to be delivered is carried on the outside of the viral particle have also been described.

"Gene delivery," "gene transfer," and the like as used herein, are terms referring to the introduction of an exogenous polynucleotide (sometimes referred to as a "transgene"), e.g., via a recombinant virus, into a host cell or by a genetically modified donor cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, iontophoresis, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art.

By "transgene" is meant any piece of a nucleic acid molecule (for example, DNA) which is inserted by artifice into a cell either transiently or permanently, and becomes part of the cell if integrated into the genome or maintained extrachromosomally. Such a transgene may include a gene which is partly or entirely heterologous (i.e., foreign) to the transgenic organism, or may represent a gene homologous to an endogenous gene of the organism.

By "transgenic cell" or "genetically modified cell" is meant a cell containing a transgene. For example, a stem cell transformed with a vector containing an expression cassette can be used to produce a population of cells having altered phenotypic characteristics.

A cell has been "transformed", "transduced", or "transfected" by exogenous or heterologous nucleic acids when such nucleic acids have been introduced inside the cell. Transforming DNA may or may not be integrated (covalently linked) with chromosomal DNA making up the genome of the cell. In prokaryotes, yeast, and mammalian cells for example, the transforming DNA may be maintained on an episomal element, such as a plasmid. In a eukaryotic cell, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations (e.g., at least about 10).

The term "wild-type" refers to a gene or gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "heterologous" as it relates to nucleic acid sequences such as gene sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature, i.e., a heterologous promoter. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention.

By "DNA" is meant a polymeric form of deoxyribonucleotides (adenine, guanine, thymine, or cytosine) in double-stranded or single-stranded form found, inter alia, in linear DNA molecules (e.g., restriction fragments), viruses, plasmids, and chromosomes. In discussing the structure of particular DNA molecules, sequences may be described herein according to the normal convention of giving only the sequence in the 5' to 3' direction along the nontranscribed strand of DNA (i.e., the strand having the sequence complementary to the mRNA). The term captures molecules that include the four bases adenine, guanine, thymine, or cytosine, as well as molecules that include base analogues which are known in the art.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or polynucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation stimulations are located 3' or downstream of the coding region.

A "gene," "polynucleotide," "coding region," or "sequence" which "encodes" a particular gene product, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. Thus, a gene includes a polynucleotide which may include a full-length open reading frame which encodes a gene product (sense orientation) or a portion thereof (sense orientation) which encodes a gene product with substantially the same activity as the gene product encoded by the full-length open reading frame, the complement of the polynucleotide, e.g., the complement of the full-length open reading frame (antisense orientation) and optionally linked 5' and/or 3' noncoding sequence(s) or a portion thereof, e.g., an oligonucleotide, which is useful to inhibit transcription, stability or translation of a corresponding mRNA. A transcription termination sequence will usually be located 3' to the gene sequence.

An "oligonucleotide" includes at least 7 nucleotides, preferably 15, and more preferably 20 or more sequential nucleotides, up to 100 nucleotides, either RNA or DNA, which correspond to the complement of the non-coding strand, or of the coding strand, of a selected mRNA, or which hybridize to the mRNA or DNA encoding the mRNA and remain stably bound under moderately stringent or highly stringent conditions, as defined by methods well known to the art, e.g., in Sambrook et al., A Laboratory Manual, Cold Spring Harbor Press (1989).

The term "control elements" refers collectively to promoter regions, polyadenylation stimulations, transcription termination sequences, upstream regulatory domains, origins of replication, internal ribosome entry sites ("IRES"), enhancers, splice junctions, and the like, which collectively provide for the replication, transcription, post-transcriptional processing and translation of a coding sequence in a recipient cell. Not all of these control elements need always be present so long as the selected coding sequence is capable of being replicated, transcribed and translated in an appropriate host cell.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence. Thus, a "promoter," refers to a polynucleotide sequence that controls transcription of a gene or coding sequence to which it is operably linked. A large number of promoters, including constitutive, inducible and repressible promoters, from a variety of different sources, are well known in the art.

By "enhancer element" is meant a nucleic acid sequence that, when positioned proximate to a promoter, confers increased transcription activity relative to the transcription activity resulting from the promoter in the absence of the enhancer domain. Hence, an "enhancer" includes a polynucleotide sequence that enhances transcription of a gene or coding sequence to which it is operably linked. A large number of enhancers, from a variety of different sources are well known in the art. A number of polynucleotides which have promoter sequences (such as the commonly-used CMV promoter) also have enhancer sequences.

"Operably linked" refers to a juxtaposition, wherein the components so described are in a relationship permitting them to function in their intended manner. By "operably linked" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. A promoter is operably linked to a coding sequence if the promoter controls transcription of the coding sequence. Although an operably linked promoter is generally located upstream of the coding sequence, it is not necessarily contiguous with it. An enhancer is operably linked to a coding sequence if the enhancer increases transcription of the coding sequence. Operably linked enhancers can be located upstream, within or downstream of coding sequences. A polyadenylation sequence is operably linked to a coding sequence if it is located at the downstream end of the coding sequence such that transcription proceeds through the coding sequence into the polyadenylation sequence. "Operably linked" with reference to peptide and/or polypeptide molecules is meant that two or more peptide and/or polypeptide molecules are connected in such a way as to yield a single polypeptide chain, i.e., a fusion polypeptide, having at least one property of each peptide and/or polypeptide component of the fusion. Thus, a stimulation or targeting peptide sequence is operably linked to another protein if the resulting fusion is secreted from a cell as a result of the presence of a secretory stimulation peptide or into an organelle as a result of the presence of an organelle targeting peptide.

"Homology" refers to the percent of identity between two polynucleotides or two polypeptides. The correspondence between one sequence and to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single strand-specific nuclease(s), and size determination of the digested fragments. Two DNA, or two polypeptide, sequences are "substantially homologous" to each other when at least about 80%, preferably at least about 90%, and most preferably at least about 95% of the nucleotides, or amino acids, respectively match over a defined length of the molecules, as determined using the methods above.

By "mammal" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like. An "animal" includes vertebrates such as mammals, avians, amphibians, reptiles and aquatic organisms including fish.

By "derived from" is meant that a nucleic acid molecule was either made or designed from a parent nucleic acid molecule, the derivative retaining substantially the same functional features of the parent nucleic acid molecule, e.g., encoding a gene product with substantially the same activity as the gene product encoded by the parent nucleic acid molecule from which it was made or designed.

By "expression construct" or "expression cassette" is meant a nucleic acid molecule that is capable of directing transcription. An expression construct includes, at the least, a promoter. Additional elements, such as an enhancer, and/or a transcription termination stimulation, may also be included.

The term "exogenous," when used in relation to a protein, gene or nucleic acid, e.g., polynucleotide, in a cell or organism refers to a protein, gene, or nucleic acid which has been introduced into the cell or organism by artificial or natural means, or in relation to a cell refers to a cell which was isolated and subsequently introduced to other cells or to an organism by artificial or natural means (a "donor" cell). An exogenous nucleic acid may be from a different organism or cell, or it may be one or more additional copies of a nucleic acid which occurs naturally within the organism or cell. An exogenous cell may be from a different organism, or it may be from the same organism. By way of a non-limiting example, an exogenous nucleic acid is in a chromosomal location different from that of natural cells, or is otherwise flanked by a different nucleic acid sequence than that found in nature.

The term "isolated" when used in relation to a nucleic acid, peptide, polypeptide or virus refers to a nucleic acid sequence, peptide, polypeptide or virus that is identified and separated from at least one contaminant nucleic acid, polypeptide, virus or other biological component with which it is ordinarily associated in its natural source. Isolated nucleic acid, peptide, polypeptide or virus is present in a form or setting that is different from that in which it is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid molecule may be present in single-stranded or double-stranded form. When an isolated nucleic acid molecule is to be utilized to express a protein, the molecule will contain at a minimum the sense or coding strand (i.e., the molecule may single-stranded), but may contain both the sense and anti-sense strands (i.e., the molecule may be double-stranded).

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "peptide", "polypeptide" and protein" are used interchangeably herein unless otherwise distinguished to refer to polymers of amino acids of any length. These terms also include proteins that are post-translationally modified through reactions that include glycosylation, acetylation and phosphorylation.

A molecule that binds a "cardiac specific antigen" includes a polypeptide (e.g., an antibody) that specifically binds to a cardiac antigen. A cardiac specific antigen may be an antigen expressed on the surface of cardiac cells or may be an antigen that is not on the surface of uninjured cardiac cells, but is exposed or expressed after an injury to cardiac tissue (e.g., ischemic injury or another injury induced by a lack of oxygen to cardiac tissue). The cardiac antigens may be exclusively expressed in injured cardiac tissue.

A molecule that binds a "stem cell specific antigen" or a "precursor cell specific antigen" includes a polypeptide (e.g., an antibody) that specifically binds to an antigen that is expressed on the surface of a stem or precursor cell. Stem cells are pluripotent or multipotent cells that can differentiate into multiple cell types. Stem cells also include cells that can transdifferentiate into at least one other cell type. A "precursor cell" or "progenitor cell" can be any cell in a specific differentiation pathway that is capable of differentiating into a more mature cell. A "differentiated cell" is a cell which is not capable of differentiating into a more mature cell under normal physiological conditions. As such, the term "precursor cell population" refers to a group of cells capable of developing into a more mature cell. A precursor cell population can comprise cells that are totipotent, cells that are pluripotent and cells that are stem cell lineage restricted (i.e., cells capable of developing into less than all hematopoietic lineages, or into, for example, only cells of erythroid lineage). As used herein, the term "totipotent cell" refers to a cell capable of developing into all lineages of cells. Similarly, the term "totipotent population of cells" refers to a composition of cells capable of developing into all lineages of cells. Also as used herein, the term "pluripotent cell" refers to a cell capable of developing into a variety (albeit not all) lineages and are at least able to develop into all hematopoietic lineages (e.g., lymphoid, erythroid, and thrombocytic lineages). For example, a pluripotent cell can differ from a totipotent cell by having the ability to develop into all cell lineages except endothelial cells. A "pluripotent population of cells" refers to a composition of cells capable of developing into less than all lineages of cells but at least into all hematopoietic lineages. As such, a totipotent cell or composition of cells is less developed than a pluripotent cell or compositions of cells. As used herein, the terms "develop", "differentiate" and "mature" all refer to the progression of a cell from the stage of having the potential to differentiate into at least two different cellular lineages to becoming a specialized cell. Such terms can be used interchangeably for the purposes of the present application.

Stem cells or precursor cells include but are not limited to, e.g., peripheral blood stem cells (PBSC), stem cells isolated from bone marrow (bone marrow cells; BMCs); stem cells isolated from adipose tissue; mesenchymal stem cells (MSCs), stem cells isolated from umbilical cord blood, menstrual fluid, cardiac derived cells, embryonic stem cells, $CD30^+$ cells, $CD34^+$ cells, $CD34^-$ cells, $CD9^+$ cells, $CD29^+$ cells, $CD44^+$ cells, $CD45^+$ cells, $CD49^+$ cells, $CD54^+$ cells, $CD56^+$ cells, $CD59^+$ cells, $CD71^+$ cells, $CD90^+$ cells, e.g., $CD90.1^+$ or $CD90.2^+$ cells, $CD105^+$ cells, $CD133^+$ cells, $CD135^+$ (flt-$3^+$) cells, $CD140a^+$ cells, $CDCP1^+$ cells, $CD146^+$ (muc-$18^+$) cells, $ABCG2^+$ cells, $CD144^+$ cells, fetal liver kinase $1^+$ cells, Stro-$1^+$ cells, $CD117^+$ (c-kit$^+$) cells, nestin$^+$ cells, PSA-NCAm$^+$ cells, $CD30^+$ cells, p75neurotophin$^+$ cells, $CD106^+$ cells, $CD120a^+$ cells, $CD124^+$ cells, $CD166^+$ cells, stem cell factor+ (SCF+) cells, Sca-$1^+$ cells, SH2$^+$ cells, SH3$^+$ cells, HLA, e.g., HLA-ABC cells, bone morphogenic protein protein+ (BMP) cells, e.g., BMP2$^+$ and BMP4$^+$ cells, Gap43$^+$ cells, glial fibrillary acidic protein$^+$ (GFAP$^+$) cells, myelin basic protein$^+$ (MBP$^+$) cells, O4$^+$ cells, O1$^+$ cells, synaptophysin$^+$ cells, alkaline phosphatase$^+$ cells, cripto$^+$ (TDGF-$1^+$) cells, podocalyxin$^+$ cells, sulfated proteoglycan$^+$ cells, e.g., silylated keratin sulfate proteoglycan$^+$ cells, stage-specific embryonic antigen$^+$ (e.g., SSEA-1, -3 and -4) cells, TRA-1-60$^+$ cells, TRA-1-81$^+$ cells, osteocalcin$^+$ cells, matrix gla protein$^+$ cells, osteopontin$^+$ cells, Thy1$^+$ cells, collagen type II$^+$ cells, collagen type IV$^+$ cells, fatty acid transporter$^+$ cells, and $\beta$-1 integrin$^+$ cells.

The term "stem cell specific antigen" or "precursor cell specific antigen" includes a protein, carbohydrate, or glycoprotein present on the surface of a stem or precursor cell. Antigens expressed on the surface of a stem cell include antigens expressed solely on the surface of a stem cell as well as antigens expressed on other cells. Different types of stem cells express different cell surface markers and therefore cells can be identified by the presence of a cell surface marker.

As used herein, "adhesion molecules" include but are not limited to selecting, mucines, integrins, e.g., LFA-1 and ICAM-1, and Ig superfamily members.

As used herein, the term "population" refers to cells having the same or different identifying characteristics. The term "lineage" refers to all of the stages of the development of a cell type, from the earliest precursor cell to a completely mature cell (i.e., a specialized cell).

The term "linked" or "conjugated" in the context of polypeptide sequences includes a linkage introduced through recombinant means or chemical means. For instance, suitable methods for chemically linking two antibodies are described in, e.g., Sen et al., *J. Hematother. Stem Cell Res.*, 10:247 (2001). Additional linkers and methods of linking antibody fragments such as scFv and dsFv are described in WO 98/41641. Additional exemplary chemical linkages include, for example, covalent bonding, including disulfide bonding; hydrogen bonding; electrostatic bonding; recombinant fusion; and conformational bonding.

The terms "effective amount" or "amount effective to" or "therapeutically effective amount" refers to an amount sufficient to induce a detectable therapeutic response in the subject. Assays for determining therapeutic responses are well known in the art. For example repair (i.e., healing) of injured myocardium can be detected using magnetic resonance imaging (MRI) to detect changes in the myocardium that are indicative of tissue regrowth and reformation.

The terms "patient", "subject" or "animal" are used interchangeably and refer to a mammalian subject to be treated, with human patients being preferred In some cases, the methods of the invention find use in experimental animals, in veterinary application, and in the development of animal models for disease, including, but not limited to, rodents including mice, rats, and hamsters; and primates.

A "drug" or "pharmaceutical" as used herein is not a molecule encoded by or produced by a vertebrate cell or a vertebrate, which in an effective amount has a therapeutic or prophylactic effect.

As used herein, "administering" or "delivering" a molecule or treatment to a cell (e.g., a molecule such as an expression vector, a delivery vehicle, an agent or treatment that enhances expression of tissue, cell or condition specific antigens, or an agent or treatment that enhances expression of adhesion molecules, and the like) includes contacting the molecule with the cell, e.g., by mixing, fusing, transducing, transfecting, microinjecting, electroporating, or shooting. For instance, for in vivo delivery, a molecule is delivered via a device such as a catheter or needle, e.g., intravenously.

General Overview

This document describes, among other things compositions, methods and devices to enhance cell therapy. In one embodiment, in order to increase the accuracy and efficiency of stem cell homing, bispecific antibodies are prepared with specificity to antigens both on the stem cell and on the target tissue, cell or site. Specific antibodies may be prepared by fusing hybridomas producing two different antibodies, or chemically linking two different antibodies, yielding antibodies that can form a tether between the stem cells and the target tissue, cell or site. The bispecific antibodies may be contacted with stem cells prior to or during cell administration (delivery), or may be separately administered. In one embodiment, the bispecific antibody comprises (Fab)'$_2$ fragments. In another embodiment, the bispecific antibody comprises scFv. In one embodiment, the bispecific antibody comprises a humanized antibody. The antibodies may be applied either systemically or via local delivery (for instance, via injection or catheter delivery). In another embodiment, administration of bispecific antibodies in the absence of exogenous donor cell, e.g., stem cell, administration may increase the homing/retention of endogenous cells. A complex of endogenous or donor cells and bispecific antibodies may allow the donor cells to establish additional contacts, firmly adhere, extravasate, and/or interact with the target tissue, cell or site, for instance, in a paracrine manner (e.g., by releasing a soluble therapeutic factor including a recombinant soluble factor).

In another embodiment, the invention provides for increased homing and retention of transplanted donor cells by manipulating the expression of adhesion molecules on the donor cells, e.g., donor stem cells, and/or endogenous tissue, e.g., endothelial cells. The increased expression allows for increased homing of donor cells to particular sites, for instance, sites of inflammation, thus increasing the efficacy of cell therapy. For example, the methods include the use of stem or other donor cells for the treatment of heart disease, such as myocardial infarction, heart failure, and cardiomyopathy, diabetes, Alzheimer's disease, spinal cord damage, arthritis, as well as other conditions. In order for cells to extravasate from the circulation and home to a specific site, they must make contact with the vessel wall, break their motion and firmly adhere. For example, an administered donor cell encounters an injured area having activated endothelium, which has increased expression of adhesion molecules such as platelet activating factor (PAF), P-selectin, and/or VAP-1, as well as optionally increased expression of cytokines, resulting in reversible binding between the donor cell and the activated endothelium. Interaction between the donor cell and activated endothelium causes activation of integrins on the donor cells, e.g., LFA-1 or Mac-1, and interaction between activated integrins and ICAM on the endothelium provides for tight binding of donor cells to the endothelium.

Further provided is the use of agents that enhance expression of adhesion molecules on donor cells and/or endogenous tissue or cells, and devices useful to deliver antibodies, donor cells, agents, or a combination thereof. In one embodiment, the invention provides a composition including a bispecific antibody which binds a stem cell specific antigen and a tissue, differentiated cell or condition associated antigen; and an agent that enhances expression of the tissue, differentiated cell or condition associated antigen. Agents useful in the methods of the invention include those which enhance cell surface molecule expression on target tissue or cells. In one embodiment, endogenous tissue is preconditioned with an agent that induces expression of VAP-1 or other molecules related to adhesion and/or inflammation such as E-selectin, ICAM-1, glycoprotein IIB, IL-2, IL-4, IL-1b, and TGF-beta.

In one embodiment, to enhance donor cell capture and extravasation after donor cell delivery into the circulation, donor cells are treated ex vivo to increase expression or activation of adhesion molecules (e.g., activated integrins). For instance, donor cells are exposed ex vivo to an activated endothelial cell surface or other surface coated with activating agents (for example, a desirable surface structure, receptors, chemokines, antibodies, peptides, and the like). In another embodiment, donor cells are treated ex vivo with one or more soluble factors such as small molecules including a peptide, e.g., chemokines, soluble receptors, or antibodies that increase adhesion molecule expression or activation. In yet another embodiment, donor cells are modified with a gene, e.g., by transfection with a plasmid encoding an adhesion molecule, yielding genetically modified donor cells. In another embodiment, donor cells are subjected to ischemic conditions, pacing, irritants, e.g., molecular components of microorganisms not found in multicellular higher eukaryotes, including but not limited to molecular components of bacterial cells such as peptidoglycans, teichoic acids, lipopolysaccharide (LPS), mannans, flagellin, pilin, and bacteria DNA, and pattern recognition molecules for viral double stranded RNA and fungal cell wall components, e.g., lipoteichoic acids, glycolipids, mannans, and zymosan, TNF-$\alpha$, or one or more cytokines, so as to increase expression or activation of adhesion molecules. In one embodiment, delivery catheter lumens may be coated with an adhesion molecule activating agent or lined with activated endothelium in order to activate the donor cells at the time of their administration.

In another embodiment, in order to enhance (increase) donor cell homing and extravasation, the target tissue for homing is exposed to an agent that enhances appropriate adhesion molecule expression on endogenous endothelial cell surfaces. For example, cytokines (e.g., TNF-$\alpha$, IFN$\gamma$, IL-6, or IL-8) or other agents, such as LPS, may be applied locally before or during the delivery of donor cells to enhance appropriate adhesion molecule expression on endogenous endothelial cell surfaces. In one embodiment, to increase bone marrow cell homing and engraftment to old infarcts, endogenous tissue may be activated by ischemic conditions, pacing, irritants, e.g., LPS, TNF-$\alpha$, cytokines or vagal nerve stimulation. In one embodiment, a delivery vehicle, e.g., a particle such as a bead, for instance, a biodegradable bead, coated with adhesion molecules is administered to a target tissue. In another embodiment, a particle that elutes cytokines is administered to a target tissue, e.g., endothelial tissue via a catheter. In one embodiment, the agent or agent containing particles are delivered by a catheter (e.g., via the coronary arteries post myocardial infarction or for angina). In another embodiment, donor cell delivery catheters may be coated with adhesion molecules or lined with activated endothelium in order to activate adhesion molecules, such as integrins, on the donor cells prior to and/or during donor cell administration.

The invention also provides methods to inhibit homing and/or extravasation of endogenous stem cells by administering an agent that blocks or inhibits binding of the adhesion molecules to a target tissue. For example, small molecule inhibitors or antibodies to adhesion molecules such as antibodies to VAP-1, selecting, or integrins, may be applied to a tissue, e.g., locally, to prevent or inhibit unwanted endogenous stem cell homing. In one embodiment, an adhesion inhibiting agent may be incorporated into a stent to prevent or reduce restenosis, e.g., to block or inhibit smooth muscle cells derived from circulating stem cells. In another embodiment, an adhesion inhibiting agent may be injected into a tumor (e.g., to prevent or inhibit angiogenesis). In yet another embodiment, an adhesion inhibiting agent may be injected into a heart (e.g., to prevent or inhibit cardiomyopathy or scarring). Thus, the invention may be useful to inhibit or treat many conditions including but not limited to myocardial infarction, heart failure, cardiomyopathy, restenosis, cancer and other diseases.

Antibodies

As used herein, the term "immunoglobulin" refers to a protein having one or more polypeptides substantially encoded by immunoglobulin genes. The recognized immunoglobulin genes include the kappa, lambda, alpha, gamma ($IgG_1$, $IgG_2$, $IgG_3$, $IgG_4$), delta, epsilon and mu constant region genes, as well as the myriad of immunoglobulin variable region genes. Full-length immunoglobulin "light chains" (about 25 kD or 214 amino acids) are encoded by a variable region gene at the amino-terminus (about 110 amino acids) and a kappa or lambda constant region gene at the carboxy-terminus. Full-length immunoglobulin "heavy chains" (about 50 kD or 446 amino acids), are similarly encoded by a variable region gene (about 116 amino acids) and one of the other aforementioned constant region genes, e.g., gamma (encoding about 330 amino acids). Heavy chains are classified as gamma, mu, alpha, delta, or epsilon, which in turn define the immunoglobulin classes, IgG, IgM, IgA, IgD and IgE, respectively. An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain (VH) refer to these light and heavy chains respectively. In each pair of the tetramer, the light and heavy chain variable regions are together responsible for binding to an antigen, and the constant regions are responsible for the antibody effector functions. In addition to antibodies, immunoglobulins may exist in a variety of other forms including, for example, Fv, Fab and $F(ab')_2$, as well as bifunctional hybrid antibodies (e.g., Lanzavecchia et al., *Eur. J. Immunol.*, 17:105 (1987)) and in single chains (e.g., Huston et al., *Proc. Natl. Acad. Sci. U.S.A.*, 85:5879 (1988) and Bird et al., *Science*, 242:423426 (1988), which are incorporated herein by reference). (See, generally, Hood et al., "Immunology", Benjamin, N.Y., $2^{nd}$ ed. (1984), and Hunkapiller and Hood, *Nature*, 323:15 (1986), which are incorporated herein by reference). Thus, the term "antibody" includes antibody fragments, as are known in the art, including Fab, $Fab_2$, single chain antibodies (scFv for example), chimeric antibodies, etc., either produced by the modification of whole antibodies or those synthesized de novo using recombinant DNA technologies.

An immunoglobulin light or heavy chain variable region consists of a "framework" region interrupted by three hypervariable regions, also called CDR's. The extent of the framework region and CDR's have been precisely defined (see, "Sequences of Proteins of Immunological Interest," E. Kabat et al., U.S. Department of Health and Human Services, (1983); which is incorporated herein by reference). The sequences of the framework regions of different light or heavy chains are relatively conserved within a species. As used herein, a "human framework region" is a framework region that is substantially identical (about 85% or more, usually 90-95% or more) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen.

Chimeric antibodies are antibodies whose light and heavy chain genes have been constructed, typically by genetic engineering, from immunoglobulin variable and constant region genes belonging to different species. For example, the variable segments of the genes from a mouse monoclonal antibody may be joined to human constant segments, such as gamma 1 and gamma 3. One example of a chimeric antibody is one composed of the variable or antigen-binding domain from a mouse antibody and the constant or effector domain from a human antibody, although other mammalian species may be used.

As used herein, the term "humanized" immunoglobulin refers to an immunoglobulin having a human framework region and one or more CDR's from a non-human (usually a mouse or rat) immunoglobulin. The non-human immunoglobulin providing the CDR's is called the "donor" and the human immunoglobulin providing the framework is called the "acceptor." Constant regions need not be present, but if they are, they are generally substantially identical to human immunoglobulin constant regions, i.e., at least about 85-90%, preferably about 95% or more identical. Hence, all parts of a humanized immunoglobulin, except possibly the CDR's, are substantially identical to corresponding parts of natural human immunoglobulin sequences. A "humanized antibody" is an antibody comprising a humanized light chain and a humanized heavy chain immunoglobulin. One says that the donor antibody has been "humanized", by the process of "humanization", because the resultant humanized antibody is expected to bind to the same antigen as the donor antibody that provides the CDR's.

Thus, humanized forms of non-human (e.g., murine) antibodies are chimeric immunoglobulins, immunoglobulin chains or fragments thereof (such as Fv, Fab, Fab', F(ab")2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody has substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will include at least a portion of an immunoglobulin constant region (Fc), typically that of a human immunoglobulin (Jones et al., *Nature*, 321:522 (1986); Riechmann et al., *Nature*, 332:323 (1988); and Presta, *Curr. Op. Struct. Biol.*, 2:593 (1992)).

It is understood that the humanized antibodies may have additional conservative amino acid substitutions which have substantially no effect on antigen binding or other immunoglobulin functions. By conservative substitutions are intended combinations such as gly, ala; val, ile, leu; asp, glu; asn, gln; ser, thr; lys, arg; and phe, tyr.

Humanized immunoglobulins, including humanized antibodies, have been constructed by means of genetic engineering. Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature,* 321:522 (1986); Riechmann et al., *Nature,* 332:323 (1988); Verhoeyen et al., *Science,* 239:1534 (1988)), by substituting rodent CDRs or CDR sequences for the corresponding sequences of a human antibody. Accordingly, such "humanized" antibodies are chimeric antibodies that have substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies.

Human antibodies can also be produced using various techniques known in the art, including phage display libraries (Hoogenboom and Winter, *J. Mol. Biol.,* 227:381 (1991); Marks et al., *J. Mol. Biol.,* 222:581 (1991)). The techniques of Cole et al. and Boerner et al. are also available for the preparation of human monoclonal antibodies (Cole et al., *Monoclonal Antibodies and Cancer Therapy,* Alan R. Liss, p. 77 (1985) and Boerner et al., *J. Immunol.,* 147:86 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10:779 (1992); Lonberg et al., *Nature,* 368:856 (1994); Morrison, *Nature,* 368:812 (1994); Fishwild et al., *Nature Biotechnology,* 14:845 (1996); Neuberger, *Nature Biotechnology,* 14:826 (1996); Lonberg and Huszar, *Intern. Rev. Immunol.,* 13:65 (1995). Most humanized immunoglobulins that have been previously described have a framework that is identical to the framework of a particular human immunoglobulin chain and three CDR's from a non-human donor immunoglobulin chain.

A framework may be one from a particular human immunoglobulin that is unusually homologous to the donor immunoglobulin to be humanized, or a consensus framework derived from many human antibodies. For example, comparison of the sequence of a mouse heavy (or light) chain variable region against human heavy (or light) variable regions in a data bank (for example, the National Biomedical Research Foundation Protein Identification Resource) shows that the extent of homology to different human regions varies greatly, typically from about 40% to about 60-70%. By choosing one of the human heavy (respectively light) chain variable regions that is most homologous to the heavy (respectively light) chain variable region of the other immunoglobulin, fewer amino acids will be changed in going from the one immunoglobulin to the humanized immunoglobulin. The precise overall shape of a humanized antibody having the humanized immunoglobulin chain may more closely resemble the shape of the donor antibody, also reducing the chance of distorting the CDR's.

Typically, one of the 3-5 most homologous heavy chain variable region sequences in a representative collection of at least about 10 to 20 distinct human heavy chains is chosen as acceptor to provide the heavy chain framework, and similarly for the light chain. Preferably, one of the 1-3 most homologous variable regions is used. The selected acceptor immunoglobulin chain may have at least about 65% homology in the framework region to the donor immunoglobulin.

In many cases, it may be considered preferable to use light and heavy chains from the same human antibody as acceptor sequences, to be sure the humanized light and heavy chains will make favorable contacts with each other. Regardless of how the acceptor immunoglobulin is chosen, higher affinity may be achieved by selecting a small number of amino acids in the framework of the humanized immunoglobulin chain to be the same as the amino acids at those positions in the donor rather than in the acceptor.

Humanized antibodies generally have advantages over mouse or in some cases chimeric antibodies for use in human therapy: because the effector portion is human, it may interact better with the other parts of the human immune system (e.g., destroy the target cells more efficiently by complement-dependent cytotoxicity (CDC) or antibody-dependent cellular cytotoxicity (ADCC)); the human immune system should not recognize the framework or constant region of the humanized antibody as foreign, and therefore the antibody response against such an antibody should be less than against a totally foreign mouse antibody or a partially foreign chimeric antibody.

DNA segments having immunoglobulin sequences typically further include an expression control DNA sequence operably linked to the humanized immunoglobulin coding sequences, including naturally-associated or heterologous promoter regions. Preferably, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and, as desired, the collection and purification of the humanized light chains, heavy chains, light/heavy chain dimers or intact antibodies, binding fragments or other immunoglobulin forms may follow (see, S. Beychok, Cells of Immunoglobulin Synthesis, Academic Press, New York, (1979), which is incorporated herein by reference).

Other "substantially homologous" modified immunoglobulins to the native sequences can be readily designed and manufactured utilizing various recombinant DNA techniques well known to those skilled in the art. For example, the framework regions can vary at the primary structure level by several amino acid substitutions, terminal and intermediate additions and deletions, and the like. Moreover, a variety of different human framework regions may be used singly or in combination as a basis for the humanized immunoglobulins of the present invention. In general, modifications of the genes may be readily accomplished by a variety of well-known techniques, such as site-directed mutagenesis (see, Gillman and Smith, *Gene,* 8:81 (1979) and Roberts et al., *Nature,* 328:731 (1987), both of which are incorporated herein by reference). Substantially homologous immunoglobulin sequences are those which exhibit at least about 85% homology, usually at least about 90%, and preferably at least about 95% homology with a reference immunoglobulin protein.

Alternatively, polypeptide fragments comprising only a portion of the primary antibody structure may be produced, which fragments possess one or more immunoglobulin activities (e.g., antigen binding). These polypeptide fragments may be produced by proteolytic cleavage of intact antibodies by methods well known in the art, or by inserting stop codons at the desired locations in vectors known to those skilled in the art, using site-directed mutagenesis.

Bispecific Antibodies

Bispecific antibodies are antibodies that have binding specificities for at least two different antigens, and may be monoclonal, and preferably human or humanized, antibodies. One of the binding specificities is for an antigen on the surface of a stem or progenitor cell, e.g., a stem cell capable of differentiating into cardiac tissue, neurons or microglial cells, beta islet cells, endothelial cells, or other more differentiated cells, synovial fluid secreting cells, cartilage, and the like. The second binding target is an antigen on host (endogenous) tissue, for instance, cardiac tissue, neurons or microglial cells, pancreatic cells, cells lining the blood vessels, or joint tissue.

Methods for making bispecific antibodies are known in the art. Traditionally, the recombinant production of bispecific antibodies is based on the co-expression of two immunoglobulin heavy chain/light chain pairs, where the two heavy chains have different specificities (Milstein and Cuello, Nature, 305:537 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829 and in Traunecker et al., EMBO J., 10:3655 (1991).

Antibody variable domains with the desired binding specificities (antibody-antigen combining sites) can be fused to immunoglobulin constant domain sequences. The fusion preferably is with an immunoglobulin heavy chain constant domain, comprising at least part of the hinge, CH2, and CH3 regions. It is preferred to have the first heavy chain constant region (CH1) containing the site necessary for light chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers that are recovered from recombinant cell culture. The preferred interface comprises at least a part of the CH3 region of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies can be prepared as full length antibodies or antibody fragments (e.g., F(ab')$_2$ bispecific antibodies). Techniques for generating bispecific antibodies from antibody fragments have been described. For example, bispecific antibodies can be prepared using a chemical linkage. Brennan et al., Science, 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody.

Additionally, Fab' fragments can be directly recovered from E. coli and chemically coupled to form bispecific antibodies. Shalaby et al., J. Exp. Med., 175:217 225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148(5):1547 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol., 152:5368 (1994). Single chain antibodies are typically recombinant polypeptides consisting of a variable light chain portion covalently attached through a linker molecule to the corresponding variable heavy chain portion, as disclosed in U.S. Pat. Nos. 5,455,030, 5,260,203, and 4,496,778, hereby incorporated by reference. A more complex construct for a single chain bispecific antibody also containing an Fc portion is provided in detail in U.S. Pat. No. 5,637,481. The principal advantage of constructs of this type is that only one species of antibody is produced, rather than three separate antibody types in the fused cell hybrid-hybridoma, which require further purification.

Antibodies with more than two valencies are contemplated. For example, trispecific antibodies can be prepared. Tutt et al., J. Immunol., 147:60 (1991).

Bispecific antibodies combining a CDR specific for stem or donor cell surface antigen and the CDR for a tissue, cell site or condition specific antigen, may also be humanized, either by replacing the light and heavy chain constant regions of the murine antibody with their human counterparts, or by grafting the CDRs onto a human antibody. Methods for carrying out these procedures are contained in U.S. Pat. Nos. 5,530,101 and 5,585,089.

Heteroconjugate antibodies are also within the scope of the present invention. Heteroconjugate antibodies are composed of two covalently joined antibodies (U.S. Pat. No. 4,676,980; and WO 91/00360). One method is by chemical heteroconjugation of two monoclonal antibodies. Chemical heteroconjugates can be created by the chemical linking of either intact antibodies or antibody fragments of different specificities. It is contemplated that the antibodies can be prepared in vitro using known methods in synthetic protein chemistry, including those involving crosslinking agents. For example, linked molecules can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

Methods for chemically conjugating two heterologous polypeptides (e.g., two antibodies are well known in the art. For example, Sen et al., *J Hemathotherapy & Stem Cell Res.*, 10:247 (2001) discloses conjugation of antibodies using 2-iminothiolane HCL (Traut's reagent) and sulphosuccinimidyl 4-(N-maleimidomethyl cyclohexane-1-carboxylate. In addition, the polypeptides can be linked using a coupling reagent such as, e.g., a carbodiimide, maleimidobenzoyl-N-hydroxysuccinimide ester (MBS), or beta-maleimidopropionic acid N-hydroxysuccinimide ester (MPS), or succinic anhydride. Other methods of linking two polypeptides include, e.g., direct covalent fusion or cross-linking with glutaraldehyde. In a preferred embodiment, a (Fab')$_2$ fragment that specifically binds to a cardiac antigen is conjugated to a (Fab')$_2$ fragment that specifically binds to the stem cell antigen CD45. In some embodiments, intact antibodies can be conjugated to each other, e.g., via their Fc domains.

Methods for linking two heterologous polypeptides recombinantly (e.g., two antibodies; two antibody fragments, including two scFv or a combination thereof) are well known in the art and are disclosed in, e.g., Sambrook et al., Molecular Cloning, A Laboratory Manual ($2^{nd}$ ed. 1989); Kriegler, Gene Transfer and Expression: A Laboratory Manual (1990); and Current Protocols in Molecular Biology (Ausubel et al., eds., 1994); Bruenke et al., *Br. J. Haematol.*, 125(2):167 (2004); Kipriyanov et al., *J. Mol. Biol.*, 330:99-111 (2003); Kriangkum et al., *Biomol. Eng.*, 18:31 (2001); Todorovska et al.; *J. Immunol. Methods*, 1:248(1-2):47 (2001); and Pluckthun and Pack, *Immunotechnology*, 3:83 (1997); e.g., Kostelny et al., *J. Immunol.*, 148:1547 (1992); Pack and Pluckthun, *Biochemistry*, 31:1579 (1992); Zhu et al., *Protein Sci.*, 6:781 (1997); Hu et al., *Cancer Res.*, 56:3055 (1996), Adams et al., *Cancer Res.*, 53:4026 (1993); and McCartney et al., *Protein Eng.*, 8:301 (1995)).

The bispecific antibodies specifically recognize and bind a desired component or epitope on the surface of donor cells, e.g., autologous, allogenic or xenogeneic donor cells. The component or epitope may be naturally occurring or one expressed from an expression cassette introduced to the donor cells (genetically altered donor cells). The bispecific antibodies also bind an antigen on target cells in endogenous tissue.

In one embodiment, the antibody is specific for fetal liver kinase-1 (Flk1), vascular endothelial cell cadherin, bone-specific alkaline phosphatase (BAP), osteocalcin (OC), bone morphogenetic protein receptor (BMPR), CD34, CD34$^+$ Sca1$^+$ Lin$^-$, CD44, c-Kit, stem cell factor (SCF), leukocyte common antigen (CD45), Muc-18 (CD146), stem cell antigen (Sca-1), stro-1 antigen, Thy-1, collagen type II, collagen type IV, sulfated proteoglycan, fatty acid transporter (FAT), beta-1 integrin, CD133, glial fibrillary acidic protein (GFAP), myelin basic protein (MPB), O4, O1, synaptophysin, alkaline phosphatase, CD9, CD30, CD56, cripto (TDGF-1), GCTM-2, neuronal cell-adhesion molecule, stage-specific embryonic antigen-3, stage-specific embryonic antigen-4, TRA-1-60, and TRA-1-81. In one embodiment, more than on bispecific antibody is employed, e.g., one specific for CD34 and VCAM, and another for Sca1 and VCAM.

In another embodiment, the antibody binds to a cell surface receptor such as insulin receptor (insulin), insulin-like growth factor receptor (including both IGF-1 and IGF-2), growth hormone receptor, glucose transporters (particularly GLUT 4 receptor), transferrin receptor, epidermal growth factor (EGF) receptor, low density lipoprotein receptor, high density lipoprotein receptor, leptin receptor, estrogen receptor; interleukin receptors including IL-1, IL-2, IL-3, IL-4, IL-5, IL-6, IL-7, IL-8, IL-9, IL-11, IL-12, IL-13, IL-15, and IL-17 receptor, VEGF receptor (VEGF), PDGF receptor (PDGF), transforming growth factor receptor (including TGF-α and TGF-β), EPO receptor (EPO), TPO receptor (TPO), ciliary neurotrophic factor receptor, prolactin receptor, and T-cell receptors. Hormones include both steroid hormones and proteinaceous hormones, including, but not limited to, epinephrine, thyroxine, oxytocin, insulin, thyroid-stimulating hormone, calcitonin, chorionic gonadotropin, corticotropin, follicle-stimulating hormone, glucagon, leuteinizing hormone, lipotropin, melanocyte-stimutating hormone, norepinephrine, parathryroid hormone, thyroid-stimulating hormone (TSH), vasopressin, enkephalins, seratonin, estradiol, progesterone, testosterone, cortisone, and glucocorticoids and the hormones listed above. Receptor ligands include ligands that bind to receptors such as cell surface receptors, which include hormones, lipids, proteins, glycoproteins, signal transducers, growth factors, cytokines, and others.

Exemplary bispecific antibodies include but are not limited to those that bind CD34, CD133, ABCG2, Sca-1, Stro-1, nestin, PSA-NCam, P75neurotrophin, c-kit, CD30, inflammatory markers such as VAP-1, P-selectin, ICAM, VCAM, VLA, collagen, cardiac tissue, pancreatic tissue, e.g., beta islet cells, neuronal tissue, microglial cells, cartilage, endothelial cells lining the blood vessels, and the like, or any combination thereof.

In another embodiment, for example, in treating restenosis, the bispecific antibody or fragment thereof is specific for progenitor endothelial cell surface antigens such as CD133, CD34, CDw90, CD117, HLA-DR, VEGFR-1, VEGFR-2, Muc-18 (CD146), CD130, stem cell antigen (Sca-1), stem cell factor 1 (SCF/c-Kit ligand), Tie-2, HAD-DR, or any combination thereof.

In one embodiment, for vascular calcifications the bispecific antibody or fragment thereof is specific for osteopontin, matrix Gla protein (MGP) or osteocalcin.

Potential Donor Cells and Exemplary Isolation Thereof

A cell population useful in the present invention is one which is capable of developing into cells of mesodermal cell lineage, ectodermal cell lineage and/or endodermal cell lineage. As used herein, mesodermal cells include cells of connective tissue, bone, cartilage, muscle, blood and blood vessel, lymphatic and lymphoid organ, notochord, pleura, pericardium, peritoneum, kidney and gonad. Ectodermal cells include epidermal tissue cells, such as those of nail, hair, glands of the skin, the nervous system, the external sense organs (e.g., eyes and ears) and mucous membranes (such as those of the mouth and anus). Endodermal cells include cells of the epithelium such as those of the pharynx, respiratory tract (except the nose), digestive tract, bladder and urethra cells. In one embodiment, cells within a stem cell population for use in the present invention include cells of at least one of the following cellular lineages: hematopoietic cell lineage, endothelial cell lineage, epithelial cell lineage, muscle cell lineage and/or neural cell lineage or having the potential to differentiate into one or more of these lineages.

A variety of stem and progenitor cell populations may be used for repair of tissue. Each cell type has its own profile of advantages. For instance, unfractionated bone marrow cells (BMCs) contain different stem and progenitor cell populations, including HSCs, endothelial progenitor cells (EPCs), and mesenchymal stem cells (MSCs). Ease of harvest and lack of extensive requirement for ex vivo manipulation are advantages of using unselected BMCs.

EPCs were originally defined by their cell surface expression of the hematopoietic marker proteins CD133 and CD34 and the endothelial marker vascular endothelial growth factor receptor-2, and their capacity to incorporate into sites of neovascularization and to differentiate into endothelial cells in situ (Asahara, *Am. J. Physiol. Cell Physiol.*, 287:C572 (2004)). Increasing evidence suggests that culture-expanded EPCs also contain a CD14$^+$/CD34$^-$-mononuclear cell population with "EPC capacity," which mediates its angiogenic effects by releasing paracrine factors (Rehman et al., *Circulation*, 107:1165 (2003); Urbich et al., *Circ. Res.*, 95:343 (2004)).

The cell surface antigen CD133 is expressed on early HSCs and EPCs, both of which collaborate to promote vascularization of ischemic tissues (Rafii et al., *Nat. Med.*, 2:702 (2003)). CD133$^+$ cells can integrate into sites of neovascularization and differentiate into mature endothelial cells. Because CD133 expression is lost on myelomonocytic cells, this marker provides an effective means to distinguish "true" CD133$^+$ EPCs from EPCs of myelomonocytic origin (Rehman et al., supra). Less than 1% of nucleated BMCs are CD133$^+$, and because these cells cannot be expanded ex vivo, only limited numbers of CD133$^+$ cells can be obtained for therapeutic purposes.

MSCs represent a rare population of CD34$^-$ and CD133$^-$ cells present in bone marrow stroma (10-fold less abundant than HSCs) and other mesenchymal tissues (Pittenger et al., *Circ. Res.*, 95:9 (2004)). MSCs can readily differentiate into osteocytes, chondrocytes, and adipocytes. Differentiation of MSCs to cardiomyocyte-like cells has been observed under specific culture conditions and after injection into healthy or infarcted myocardium in animals (Makino et al., *J. Clin. Invest.*, 103:697 (1999); Toma et al., *Circulation*, 105:93 (2002); Mangi et al., *Nat. Med.*, 9:1195 (2003)). When injected into infarct tissue, MSCs may enhance regional wall motion and prevent remodeling of the remote, noninfarcted myocardium (Mangi et al., 2003; Shake et al., *Ann. Thorac. Surg.*, 73:1919 (2002). Cultured MSCs secrete angiogenic cytokines, which improve collateral blood flow recovery in a murine hind limb ischemia model (Kinnaird et al., *Circ. Res.*, 94:678 (2004)). Because MSC clones can be expanded in vitro, and reportedly have a low immunogenicity, they may be used in an allogeneic setting (Pittenger et al., *Circ. Res.*, 95:9 (2004)).

Skeletal myoblasts, or satellite cells, are progenitor cells that normally lie in a quiescent state under the basal membrane of mature muscular fibers. Myoblasts can be isolated from skeletal muscle biopsies and expanded in vitro. Myoblasts differentiate into myotubes and retain skeletal muscle properties when transplanted into an infarct scar (Ghostine et al., *Circulation*, 106:I131 (2002); Murry et al., *J. Clin. Invest.*, 98:2512 (1996); Leobon et al., *Proc. Natl. Acad. Sci. USA*, 100:7808 (2003); Pagani et al., *J. Am. Coll. Cardiol.*, 41:879 (2003)). Myoblast transplantation has been shown to augment systolic and diastolic performance in animal models of myocardial infarction (Dowell et al., *Cardiovasc. Res.*, 58:336 (2003)).

Resident cardiac stem cell (CSC) population(s) are capable of differentiating into cardiomyocyte or vascular lineages (Hierlihy et al., *FEBS Lett.*, 530:239 (2002); Beltrami et al., *Cell*, 114:763 (2003); Oh et al., *Proc. Natl. Acad. Sci. USA*, 100:12313 (2003); Martin et al., *Dev. Biol.*, 265:262 (2004); Messina et al., *Circ. Res.*, 95:911 (2004)). Intriguingly, CSCs can be clonally expand from human myocardial biopsies (Messina et al., 2004). It has been reported that intramyocardial injection of these cells after AMI in mice promotes cardiomyocyte and vascular cell formation and leads to an improvement in systolic function (Messina et al., 2004).

Embryonic stem (ES) cells are totipotent stem cells derived from the inner cell mass of blastocysts. Under specific culture conditions, ES cells differentiate into multicellular embryoid bodies containing differentiated cells from all three germ layers including cardiomyocytes. Human ES cell-derived cardiomyocytes display structural and functional properties of early-stage cardiomyocytes that couple electrically with host cardiomyocytes when transplanted into normal myocardium (Kehat et al., *J. Clin. Invest.*, 108:407 (2001); Kehat et al., *Nat. Biotechnol.*, 22:1282 (2004)). Nuclear transfer techniques provide a means for generating an unlimited supply of histocompatible ES cells for the treatment of cardiac disease (therapeutic cloning) (Lanza et al., *Circ. Res.*, 94:820 (2004)).

Donor cells within the scope of the invention include but are not limited to bone marrow-derived cells, e.g., mesenchymal cells and stromal cells, smooth muscle cells, fibroblasts, SP cells, pluripotent cells or totipotent cells, e.g., teratoma cells, hematopoietic stem cells, for instance, cells from cord blood and isolated CD34$^+$ cells, multipotent adult progenitor cells, adult stem cells, embyronic stem cells, skeletal muscle derived cells, for instance, skeletal muscle cells and skeletal myoblasts, cardiac derived cells, myocytes, e.g., ventricular myocytes, atrial myocytes, SA nodal myocytes, AV nodal myocytes, and Purkinje cells. The term "donor cell" includes embryonic, fetal, pediatric, or adult cells or tissues, including but not limited to, stem cells and precursors (progenitor) cells. Thus, donor cells of the invention can be myocardial cells, bone marrow cells, hematopoietic cells, lymphocytes, leukocytes, granulocytes, hepatocytes, monocytes, macrophages, fibroblasts, neural cells, mesenchymal stem cells, beta-islet cells, and combinations thereof, or cells capable of differentiating into those cells. In one embodiment, the donor cells are autologous cells, however, non-autologous cells, e.g., xenogeneic cells, may also be employed. In one embodiment, the donor cells are endothelial progenitor cells, CD133$^+$ cells, CD34$^+$ cells, mesenchymal stem cells, skeletal myoblasts, neural stem cells, pancreatic beta cells, cardiac stem cells or embryonic stem cells.

Stem cells may be isolated from any source known in the art and includes, but is not limited to, e.g., peripheral blood stem cells (PBSC), stem cells isolated from bone marrow; stem cells isolated from adipose tissue; mesenchymal stem cells, embryonic stem cells, CD34$^+$ cells, CD34$^-$ cells, CD45$^+$ cells, or combinations thereof). Stem cells which express one or more of the following antigens may be useful in the methods of the invention: CD34, CD133, ABCG2, Sca-1, Stro-1, nestin, PSA-NCAm, P75 neurotrophin, c-kit or CD30. Exemplary stem cells and methods of isolating them are described in, e.g., Fickert et al., *Osteoarthritis Cartilage*, 11:790 (2003), which discloses identification, quantification and isolation of human mesenchymal progenitor cells from osteoarthritic synovium; Meirelles et al., *Br. J. Haematol.*, 123:702 (2003), which discloses isolation, in vitro expansion, and characterization of mesenchymal stem cell from bone marrow; Pittenger et al., *Science*, 284:143 (1999), which discloses isolation, analysis, and differentiation of adult human mesenchymal stem cells from bone marrow; Lataillade et al., *Blood*, 95:756 (2000) or Handgretinger et al., *Bone Marrow Transplant*, 27:777 (2001), which disclose isolation, analysis, and purification of adult human peripheral blood CD34$^+$ progenitor cells; U.S. Pat. No. 6,667,034 which discloses isolation and differentiation of stem cells from human hematopoietic cells, i.e., from bone marrow and peripheral blood; and U.S. Pat. No. 6,261,549 which discloses isolation of human mesenchymal stem cells from peripheral blood; and Gepstein, *Circ. Res.*, 91:866 (2002), which discloses derivation of embryonic stem cells.

Typically, stem cells are purified from peripheral blood using methods known in the art including, e.g., immunomagnetic selection with the MACS system (Miltenyi Biotech, Tebu) or antibody-coated Dynabeads (Dynal Biotech, Oslo). A heterogeonus population of cells may be contacted with antibody-coated magnetic beads. The antibody specifically binds to a cell surface marker differentially or preferentially expressed on the surface of a stem cell, thereby forming a complex between the beads and the stem cells in the heterogenous population. The labeled stem cells can then be isolated from the heterogenous cell population using methods known in the art including, e.g., flow cytometry.

For example, bone marrow is aspirated from the posterior iliac crest under a brief general anesthesia. Unselected BMCs are enriched under good manufacturing practice conditions by 4% gelatin-polysuccinate density gradient sedimentation as described in Wollert et al. (*Lancet*, 364:141 (2004)). $CD34^+$ cells may be immunomagnetically enriched from unselected BMCs by the CliniMACS$^{plus}$ System and CD34 antibodies from Miltenyi Biotech. The number of CD34+ cells in unselected BMC preparations and in CD34-enriched preparations may be determined by flow cytometry analysis (FACSCalibur, BD Biosciences) using an antibody from Beckman Coulter.

Alternatively, BMCs are isolated by Ficoll density gradient centrifugation. After two washing steps, cells are resuspended to yield a heterogeneous cell population including hematopoietic progenitor cells, but also other cell types (e.g., side population cells, stromal cells, and so on). Overall, a mean value of $5.5\pm3.9\times10^6$ CD34/CD45-positive cells may be infused per patient. To assess colony-forming units, BMC ($1\times10^5$ per dish) are seeded in methylcellulose plates (Methocult GF H4535 including stem cell factor, granulocyte colony-stimulating factor, granulocyte-macrophage colony-stimulating factor, interleukin-3, interleukin-6; CellSystems, St. Katharinen, Germany). Plates are studied under phase-contrast microscopy, and colony-forming units of granulocyte-macrophage (colonies>50 cells) are counted after 14 days of incubation.

For CPCs, mononuclear cells from venous blood are suspended in medium supplemented with 1 ng/ml carrier-free human recombinant vascular endothelial growth factor (R&D, Wiesbaden, Germany), 0.1 µmol/L atorvastatin (Pfizer, Freiburg, Germany), and 20% human serum drawn from each individual patient. Cells are seeded at a density of $6.4\times10^5$ cells/mm$^2$ on fibronectin-coated dishes (Roche, Grenzach, Germany). After three days of cultivation, cells are detached with 0.5 mmol/L ethylenediamine-tetraacetic acid, washed twice, and re-suspended in a final volume of 10 ml of medium. The resulting cell suspension contains a heterogeneous population of progenitor cells, however, more than 90% of the cells show endothelial characteristics, as demonstrated by Di1-acetylated low-density lipoprotein-uptake and lectin binding and the expression of typical endothelial marker proteins including vascular endothelial growth factor-R2 (KDR) (ReliaTech, Braunschweig, Germany), endoglin (CD105) (NeoMarkers, Asbach, Germany), von Willebrand factor (Oncogene, Schwalbach, Germany), and platelet endothelial cell adhesion molecule-1 (PECAM-1/CD31) (Dianova, Hamburg, Germany) (Assmus et al., *Circulation*, 106: 3009 (2002); Dimmeler et al., *J. Clin. Invest.*, 108:391 (2001); Vasa et al., *Circulation*, 103:2885 (2001); Vasa et al., *Circ. Res.*, 89:1 (2001)).

Various techniques may be employed to separate the cells by initially removing cells of dedicated lineage. Monoclonal antibodies are particularly useful for identifying markers associated with particular cell lineages and/or stages of differentiation.

If desired, a large proportion of terminally differentiated cells may be removed by initially using a "relatively crude" separation. For example, magnetic bead separations may be used initially to remove large numbers of lineage committed cells. Desirably, at least about 80%, usually at least 70% of the total hematopoietic cells are removed.

Procedures for separation may include but are not limited to, magnetic separation, using antibody-coated magnetic beads, affinity chromatography, cytotoxic agents joined to a monoclonal antibody or used in conjunction with a monoclonal antibody, including but not limited to, complement and cytotoxins, and "panning" with antibody attached to a solid matrix, e.g., plate, elutriation or any other convenient technique.

Techniques providing accurate separation include but are not limited to, flow cytometry, which can have varying degrees of sophistication, e.g., a plurality of color channels, low angle and obtuse light scattering detecting channels, impedance channels, etc.

Donor cells can be expanded in vitro to provide an expanded population of donor cells for administration. In addition, donor cells may be treated in vitro (ex vivo) to induce certain phenotypic characteristics, e.g., to induce proliferation or differentiation, to introduce one or more expression cassettes (transgenes) encoding a gene product, i.e., the donor cells may be recombinant cells. Thus, donor cells may be primed or preconditioned, e.g., treated with a cytokine or a mixture of cytokines or transformed with an expression cassette, prior to being contacted with bispecific antibodies. Priming or preconditioning can facilitate homing of the donor cell to the tissue or site of interest and differentiation or transdifferentiation of the donor cell after it has homed to the injured tissue or site of interest.

In one embodiment, the donor cells are recombinant cells having an expression cassette. The expression cassette optionally includes at least one control element such as a promoter, optionally a constitutive promoter, an enhancer, or a transcription termination sequence. In one embodiment, a promoter is operably linked to an open reading frame encoding a gene product, e.g., a soluble therapeutic gene product or a heterologous target for a bispecific antibody, e.g., a marker or reporter such as green fluorescent protein (GFP), or a factor which induces expression of an antigen recognized by the bispecific antibody. In one embodiment, the promoter and/or enhancer is one which is cell- or tissue-specific, e.g., cardiac cell-specific.

Delivery of exogenous transgenes may be accomplished by any means, e.g., transfection with naked DNA, e.g., a vector comprising the transgene, liposomes, calcium-mediated transformation, electroporation, or transduction, e.g., using recombinant viruses. A number of transfection techniques are generally known in the art. See, e.g., Graham et al., *Virology*, 52, 456 (1973), Sambrook et al., *Molecular Cloning: A Laboratory Manual*, Cold Spring Harbor Laboratories, New York (1989), Davis et al., *Basic Methods in Molecular Biology*, Elsevier (1986) and Chu et al., *Gene*, 13, 197 (1981). Particularly suitable transfection methods include calcium phosphate co-precipitation (Graham et al., *Virol.*, 52, 456 (1973)), direct microinjection into cultured cells (Capecchi, *Cell*, 22, 479 (1980)), electroporation (Shigekawa et al., *BioTechniques*, 6, 742 (1988)), liposome-mediated gene transfer (Mannino et al., *BioTechniques*, 6, 682 (1988)), lipid-mediated transduction (Felgner et al., *Proc. Natl. Acad. Sci. USA*, 84, 7413 (1987)), and nucleic acid delivery using high-velocity microprojectiles (Klein et al., *Nature*, 327, 70 (1987)). Gene delivery vectors include, but are not limited to, isolated nucleic acid, e.g., plasmid-based vectors which may be extra-chromosomally maintained, and viral vectors, e.g., recombinant adenovirus, retrovirus, lentivirus, herpesvirus including cytomegalovirus, poxvirus, papilloma virus, or adeno-associated virus, including viral and non-viral vectors which are present in liposomes, e.g., neutral or cationic liposomes, such as DOSPA/DOPE, DOGS/DOPE or DMRIE/DOPE liposomes, and/or associated with other molecules such as DNA-anti-DNA antibody-cationic lipid (DOTMA/DOPE) complexes.

Exemplary Methods

The goal of any cell delivery strategy is to transplant sufficient numbers of cells into the region of interest and to achieve maximum retention of cells within that area. Retention may be defined as the fraction of transplanted cells retained in a target tissue or site for a period of time (minutes, hours or weeks). The local milieu is an important determinant of cell retention, as it will influence short-term cell survival and, if a transvascular approach is used, cell adhesion, transmigration through the vascular wall, and tissue invasion.

In one embodiment, bispecific antibodies and donor cells are employed to enhance cell delivery and retention. Once a bispecific antibody is provided, it can be bound to a donor cell. The bispecific antibodies can be added to donor cells in vitro (ex vivo) before donor cell administration or at the time of donor cell administration, to yield bispecific antibody-cell complexes. The bispecific antibodies may also be given independent of donor cell administration, e.g., in order to increase the homing of endogenous stem cells. The antibodies, cells, or antibody-cell complexes may be applied either systemically, e.g., intravenous administration, or via local delivery (direct injection or catheter delivery). Suitable ratios of bispecific antibody to donor cell can be selected based on the particular properties of the bispecific antibody and the donor cell. Typically about 0.05 to 500 ng, about 5 to about 400 ng, about 10 to about 300 ng, about 25 to about 250 ng, about 40 to about 100 ng, or about 50 ng of bispecific antibody per $10^6$ donor cells is sufficient to generate a population of bispecific antibody-donor cell complexes suitable for use in the methods of the invention.

One embodiment of the present invention provides a method of targeting stem cells to injured cardiac tissues. The stem cells may be autologous to the patient with the cardiovascular disorder, or may be obtained from an allogeneic or xenogeneic donor. In patients receiving BMC, bone marrow aspirates may be obtained in the morning of the day of cell transplantation. In patients receiving CPC, 250 ml of venous blood is collected immediately after randomization (24 hours after the AMI), mononuclear cells are purified and ex vivo cultured for three days, and then re-infused into the infarct artery. In one embodiment, cells, e.g., those contacted with bispecific antibodies ex vivo, may be infused via an over-the-wire balloon catheter advanced into a stent previously implanted during the acute reperfusion procedure and inflated with low pressure to completely block blood flow for 3 minutes to allow for adhesion and potential transmigration of the infused cells through endothelium. This maneuver may be repeated three times to accommodate infusion of the total 10 ml donor cell suspension, interrupted by 3 minutes of reflow by deflating the balloon to minimize extensive ischemia. After completion of intracoronary cell transplantation, coronary angiography may be repeated to ascertain vessel patency, absence of embolization, and unimpeded flow of contrast material.

In one embodiment, unselected BMCs optionally with bispecific antibodies are infused into the infarct-related artery via the central lumen of an over-the-wire balloon catheter. To maximize the contact time of the BMCs with the microcirculation of the infarct-related artery, the balloon may be inflated inside the stent for about 3 minutes during the infusion. Additionally, BMCs may be infused during 3 to 4 additional coronary occlusions. Between occlusions, the coronary artery is reperfused for about 3 minutes.

Alternatively, unselected BMCs optionally with bispecific antibodies are injected via a right antecubital vein. Additionally, cells may be infused into the infarct-related artery.

In another embodiment, about 2.5-fold more bone marrow is aspirated to obtain more $CD34^+$ cells. $CD34^+$ cells are enriched from unselected BMCs, and infused optionally with bispecific antibodies into the infarct-related artery. Afterward, the CD34-depleted BMC fraction may be infused during 3 to 4 additional coronary occlusions.

Selective intracoronary application delivers a maximum concentration of cells homogeneously to the site of injury during first passage. Unselected BMCs, circulating blood-derived progenitors cells, and MSCs have been delivered via the intracornary route in patients with AMI and ischemic cardiomyopathy. Cells are delivered through the central lumen of an over-the-wire balloon catheter during transient balloon inflations to maximize the contact time of the cells with the microcirculation of the infarct-related artery.

Exemplary Compositions

The present invention also relates to a pharmaceutical composition comprising the bispecific antibodies and/or agents that enhance tissue, cell or condition specific antigen expression in endogenous tissue in a pharmaceutically acceptable carrier. In some embodiments, the pharmaceutical compositions includes donor cells with the bispecific antibodies and agents that enhance tissue, cell or condition specific antigen expression in endogenous tissue. In some therapeutic applications, compositions are administered to a patient suffering from a disease (e.g., cardiovascular disease), in an amount sufficient to cure or at least partially arrest the disease and its complications, i.e., by repairing injured myocardium. An amount adequate to accomplish this is defined as a therapeutically effective dose. Amounts effective for this use depend on the severity of the cardiovascular disease and the general state of the patient's health.

The pharmaceutical compositions of the present invention (i.e., compositions comprising bispecific antibodies, stem cells and/or agents that enhance tissue, cell or condition specific antigen expression in endogenous tissue) may be administered by any means known in the art. Preferably, the compositions are suitable for parenteral administration (e.g., intravenous, intraperitoneal). The compositions of the invention may also be administered subcutaneously, into vascular spaces, or during surgery, e.g., by injection, or into joints, e.g., intraarticular injection such as during orthoscopic surgery.

Single or multiple administrations of the compositions may be administered depending on the dosage and frequency as required and tolerated by the patient. In any event, the composition should provide a sufficient quantity of the donor cells to effectively treat the patient, e.g., to repair or augment repair of injured myocardium.

Preferably, the compositions for administration comprise a solution of the composition and a pharmaceutically acceptable carrier, preferably an aqueous carrier. A variety of aqueous carriers can be used, e.g., buffered saline and the like.

These solutions are sterile and generally free of undesirable matter. These compositions may be sterilized by conventional, sterilization techniques known in the art. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The composition having bispecific antibodies and donor cells may also formulated in microspheres, liposomes or other microparticulate delivery systems. The concentration of composition bispecific antibodies and donor cells in these formulations can vary widely, and may be selected primarily based on fluid volumes, viscosities, body weight and the like in accordance with the particular mode of administration selected and the patient's needs.

Thus, typical pharmaceutical composition comprising bispecific antibodies for intravenous administration are about 0.05 to 500 ng, about 5 to about 400 ng, about 10 to about 300 ng, about 25 to about 250 ng, about 40 to about 100 ng, or about 50 ng of bispecific antibody per patient per day. A typical pharmaceutical composition comprising donor cells for intravenous administration may be about $10^5$ to about $4 \times 10^6$ cells, about $5 \times 10^5$ about $3 \times 10^6$ cells, or about $10^6$ to about $2.5 \times 10^6$ cells, or about $1.5 \times 10^6$ to about $2.0 \times 10^6$ cells per patient per day, or about 0.5 to about $50 \times 10^6$ cells/kg, or up to about $1 \times 10^{10}$ to about $5 \times 10^{10}$ cells per patient. Methods for preparing parenterally administrable compositions are known or apparent to those skilled in the art and are described in more detail in such publications as Remington's Pharmaceutical Science, $17^{th}$ Ed., Mack Publishing Co., Easton, Pa., (1985).

Typically, the pharmaceutical compositions having bispecific antibodies and donor cells are administered in a therapeutically effective dose over either a single day or several days by daily intravenous infusion. The dose is dependent upon the properties of the composition having bispecific antibodies and donor cells employed, e.g., its activity and biological half-life, the concentration of the composition having bispecific antibodies and donor cells in the formulation, the site and rate of dosage, the clinical tolerance of the patient involved, the extent of disease afflicting the patient and the like as is well within the skill of the physician.

The compositions may be administered in solution. The pH of the solution should be in the range of pH 5 to 9.5, preferably pH 6.5 to 7.5. The compositions thereof should be in a solution having a suitable pharmaceutically acceptable buffer such as phosphate, tris (hydroxymethyl) aminomethane-HCl or citrate and the like. Buffer concentrations should be in the range of 1 to 100 mM. The solution of the compositions may also contain a salt, such as sodium chloride or potassium chloride in a concentration of 50 to 150 mM. An effective amount of a stabilizing agent such as albumin, a globulin, a detergent, a gelatin, a protamine or a salt of protamine may also be included. In some embodiments, systemic administration of the composition having bispecific antibodies and donor cells is typically made every two to three days or once a week if a humanized form of the antibody is used. Alternatively, daily administration is useful. Usually administration is by intravascular infusion.

The compositions described herein can be administered to a patient in conjunction with other therapies, e.g., other therapies for cardiovascular disease. For example, the compositions may be administered in conjunction with angioplasty to promote repair of injured cardiac tissue. The compositions may be administered prior to the angioplasty, contemporaneous with the angioplasty, or subsequent to the angioplasty.

Agents and Treatments Useful to Modulate Homing (Localization) of Cells

Agents and treatments useful in the methods of the invention include those which alter, e.g., enhance, cell surface molecule expression on target tissue or cells, e.g., ex vivo or at a particular physiological site, or both. Agents or treatments useful in the methods of the invention include but are not limited to ischemic conditions, pacing, irritants, e.g., LPS, TNF-α or other cytokines such as IL-1, IL-6 or IL-8, including agents that enhance adhesion molecule expression or activation on donor cells, endogenous cells, or both. Agents that modulate the expression or activation of adhesion molecules, e.g., those in Table 1, or alter cell surface molecule expression on target tissue or cells include but are not limited to NSAIDS, glucocorticoids, agents that modulate, e.g., enhance or inhibit, cytokines or their receptors, peptides, e.g., RGD or KTS based peptides or their mimetics, or antibodies, i.e., neutralizing, agnostic or antagonistic antibodies specific for adhesion molecules such as selecting, ICAMS, and VCAMS (see Table 1 and Verbeuren et al., *Microcirc.*, 7:541 (2000), Wahl et al., *Curr. Op. Clin. Nutr. Meta. Care*, 2:109 (1999), Buchner et al., *Imm. Allergy Clin. North Am.*, 24:615 (2004), Lutters et al., *Curr. Op. Libidology*, 15:545 (2004)), and agents disclosed in U.S. published Applications 20060030575, 20050226873; 20050187611; 20050059669; 2005026917; 20040086519; 20040077684; 20040063934; 20040077638; 20030186967; 2003018633; 20030171368; and U.S. Pat. Nos. 6,663,863; 6,586,187; 6,541,116; 6,461, 821; 6,214,334; 6,185,953; 5,961,483; 5,935,598; 5,718,892; 5,691,423; and 5,196,403. Compounds that modulate cadherin are disclosed in U.S. Pat. Nos. 6,907,238; 6,914,144; 6,962,969; 6,806,255; 6,203,788; and 6,569,996.

In one embodiment, endogenous tissue is preconditioned with an agent or treatment that induces expression of VAP-1 or other molecules related to adhesion and/or inflammation such as E-selectin, ICAM-1, glycoprotein IIB, IL-2, IL-4, IL-1b, TGF-beta.

TABLE 1

| Adhesion molecules | Other names | Ligands |
|---|---|---|
| Selectins/ligands | | |
| P-selectin | CD62P, GMP140 | PSGL-1, Lewis X, CD24 |
| E-selectin | CD62D, ELAM1 | ESL-1, Lewis X, PSGL-1, Lyset |
| L-selectin | CD62L | Lewis X, CD 34, PSGL-1, GlyCAM |
| E-selectin ligand 1 | ESL-1 | E-selectin |
| P-selectin ligand 1 | CD162, PSGL-1 | P-, L-, E-selectin PNAd, cutaneous lymphocyte antigen (CLA), CD15 (Sialyl-Lewis X) |

TABLE 1-continued

| Adhesion molecules | Other names | Ligands |
|---|---|---|
| Ectoenzymes and other adhesion molecules | | |
| VAP-1 | semicarbazide-sensitive amino oxidase (SSAO), AOC-3, HPAO, and membrane, copper amine oxidase | amine groups |
| Retina-specific amine oxidase | AOC2 | amine groups |
| CD26 | EC3.4.14.5, adenosine deaminase binding protein, ADA binding protein, dipeptidylpeptidase IV, DPPIV ectoenzyme | adenosine deaminase, collagen, CD45 |
| CD38 | T10, ADP-ribosylcyclase; cyclic ADP-ribose hydrolase | CD31, hyaluronic acid |
| CD73 | Ecto-5'-nucleotidase | |
| mannose receptor | | |
| clever-1 (common lymphatic endothelial and vascular receptor-1) | stabilin-1, FEEL-1 | |
| CD40 | Bp50 | CD40L |
| CD44 | ECMRIII, HCAM, HUTCH-1, Hermes, Lu, In-related, Pgp-1, gp85 | Hyaluronan, MIP-1β, osteopontin, ankyrin, fibronectin |
| Immunoglobulins | | |
| ICAM-1 | CD54 | αLβ2, αMβ, αXβ2 |
| ICAM-2 | CD102 | αLβ2, αMβ |
| ICAM-3 | CD50 | αLβ2, αDβ2, DC-SIGN |
| VCAM-1 | CD106 | α4β1, α4β7 αDβ2 |
| PECAM-1 | CD31 | PECAM-1, Vβ3 |
| NCAM-1 | LFA-3 (lymphocyte function associated antigen-3), CD58 | CD2 |
| MAdCAM-1 (mucosal vascular addressin cell adhesion molecule-1) | MACAM-1, mucosal addressin cell adhesion molecule-1 precursor | |
| JAM-2 (junctional adhesion molecule-2), | C21orf43, HGNC1284, JAMA-A, JAM-B, Junctional adhesion molecule B precursor, PRO245, UNQ219/PRO245, vascular endothelial junction-associated molecule, VE-JAM, CD322 | |
| JAM-1 (junctional adhesion molecule-1) | Jcam-1, JAM-A, Jcam, Junctional adhesion molecule A precursor, F11 receptor, Ly106, AA638916, 913004G24, BV11 antigen, ESTM33, CD321 | |
| Mucins | | |
| Mad-CAM-1 | | α4β7 integrin, L-selectin |
| GlyCAM-1 (glycosylation dependent cell adhesion molecule-1) | | L-selectin |
| Integrins | | |
| Integrin α2/β1 | CD49b/CD29, VLA2 | Collagen, laminin |
| Integrin α4/β1 | CD49d/CD29, VLA4 | VCAM-1, FN |
| Integrin αL/β2 | CD11a/CD18, LFA1 | ICAMs |
| Integrin αM/β2 | CD11b/CD18, Mac1 | ICAMs, iC3b FX, FG |
| Integrin αX/β2 | CD11c/CD18 | ICAM-1, FG, iC3b, CD23 |
| Integrin αD/β2 | CD11d/CD18 | ICAM-3, VCAM-1 |
| Integrin α2B/α3 | GPIIb/IIIa | vWF, FN, FG, VN, thrombospondin |

TABLE 1-continued

| Adhesion molecules | Other names | Ligands |
|---|---|---|
| Integrin αV/β3 | VNR, CD51/CD61 | PECAM-1, WN, FN, FG, vWF, VN |
| Integrin αV/β5 | | |
| Integrin α4/β7 | | |

Devices Useful to Administer Donor Cells, Agents that Enhance Expression of Endogenous Antigens and Antibodies Devices useful for administering antibodies, and/or agents that enhance expression of endogenous antigens and/or administering or implanting donor cells into an organ or body part include a lumen, and may be, but are not limited to, a catheter, needle, stent, e.g., be made of stainless steel, Nitinol (NiTi), or chromium alloy and biodegradable materials, a stent graft, a synthetic vascular graft, e.g., one made of a cross-linked PVA hydrogel, polytetrafluoroethylene (PTFE), expanded polytetrafluoroethylene (ePTFE), porous high density polyethylene (HDPE), polyurethane, and polyethylene terephthalate, or biodegradable materials, a heart valve, a vascular prosthetic filter, a pacemaker, a pacemaker lead, a defibrillator, a patent foramen ovale (PFO) septal closure device, a vascular clip, a vascular aneurysm occluder, a hemodialysis graft, a hemodialysis catheter, an atrioventricular shunt, an aortic aneurysm graft device or components, a venous valve, a suture, a vascular anastomosis clip, an indwelling venous or arterial catheter, a vascular sheath or a drug delivery port. Preferred devices for antibody or cell delivery include but are not limited to catheters, needles and drug pumps, and may include balloons to occlude blood flow and adjustable delivery rate controls, which are biocompatible with the antibodies or cells. The medical device can be made of numerous materials depending on the device.

The device may include a biocompatible matrix formed of materials including without limitation a synthetic material such as polyurethanes, segmented polyurethane-urea/heparin, poly-L-lactic acid, cellulose ester, polyethylene glycol, polyvinyl acetate, dextran and gelatin, and/or naturally-occurring material such as basement membrane components such as collagen, elastin, laminin, fibronectin, vitronectin, heparin, fibrin, cellulose, and amorphous carbon, or fullerenes, e.g., a fullerene ranging from about $C_{20}$ to about $C_{150}$ in the number of carbon atoms, and more particularly, the fullerene is $C_{60}$ or $C_{70}$. The fullerene of the invention can also be arranged as nanotubes.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A composition, comprising:
   a bispecific antibody which binds CD34 on a mammalian stem cell and which binds an antigen on a mammalian endothelial cell, wherein the antigen is VAP-1, P-selectin, E-selectin, ICAM, VCAM or VLA; and
   an amount of TNF-α, IFNγ, IL-1, or IL-4 selected to enhance expression of the antigen in mammalian endothelial cells relative to corresponding cells in the absence of the TNF-α, IFNγ, IL-1, or IL-4.

2. The composition of claim 1 further comprising stem cells expressing CD34.

3. The composition of claim 2 wherein the stem cells are recombinantly altered stem cells.

4. A composition, comprising:
   a bispecific antibody which binds a stem cell specific antigen on a mammalian stem cell selected from CD34, CD133, ABCG2, Sca-1, Stro-1, Nestin, PSA-NCAm, p75 neurotrophin, c-kit, or CD30, and which binds VAP-1; and
   an amount of TNF-α, IFNγ, IL-1, or IL-4 selected to enhance expression of VAP-1 in mammalian endothelial cells relative to corresponding cells in the absence of the TNF-α, IFNγ, IL-1, or IL-4.

5. The composition of claim 1 or 4, which comprises TNF-α or IL-1.

6. The composition of claim 5 wherein the IL-1 is IL-1beta.

7. A method of enhancing localization and retention of stem cells, comprising:
   delivering to a mammal in need of cell therapy an effective amount of bispecific antibodies which bind CD34 and which bind VAP-1, P-selectin, E-selectin, ICAM, VCAM or VLA, an amount of TNF-α, IFNγ, IL-1, or IL-4 that enhances expression of VAP-1, P-selectin, E-selectin, ICAM, VCAM or VLA in mammalian endothelial cells, and donor mammalian stem cells having CD34.

8. The method of claim 7 wherein the bispecific antibodies are contacted with the donor stem cells prior to delivery.

9. The method of claim 7 wherein the donor stem cells are systemically delivered.

10. The method of claim 7 wherein the donor stem cells are locally delivered.

11. The method of claim 7 wherein the donor stem cells are delivered contemporaneously with the bispecific antibodies.

12. The method of claim 7 wherein the bispecific antibodies are systemically delivered.

13. The method of claim 7 wherein the bispecific antibodies are delivered via a catheter.

14. The method of claim 7 wherein the agent is locally delivered prior to the administration of the bispecific antibodies or the cells.

15. The method of claim 7 wherein the donor stem cells are bone marrow cells (BMCs) or mesenchymal stem cells (MSCs).

16. The method of claim 7 wherein the stem cells are autologous or allogenic stem cells.

17. A method for targeting stem cells to a site of injury or inflammation, comprising: delivering to a mammal having a site of injury or inflammation an effective amount of bispecific antibodies which bind CD34 on a mammalian stem cell and which bind VAP-1, P-selectin, E-selectin, ICAM, VCAM or VLA on mammalian endothelial cells, an amount of TNF-α, IFNγ, IL-1, or IL-4 that enhances expression of VAP-1, P-selectin, E-selectin, ICAM, VCAM or VLA in mammalian endothelial cells, and donor mammalian stem cells having CD34, wherein the TNF-α, IFNγ, IL-1, or IL-4 is locally delivered to the site of injury or inflammation.

18. The method of claim 7 or 17 wherein the mammal is a human.

19. The method of claim 7 or 17 wherein the IL-1 is IL-1 beta.

* * * * *